(12) United States Patent
Bayer et al.

(10) Patent No.: US 7,927,272 B2
(45) Date of Patent: Apr. 19, 2011

(54) SURGICAL PORT WITH EMBEDDED IMAGING DEVICE

(75) Inventors: Lex Bayer, Palo Alto, CA (US); Jack Higgins, Los Altos, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 900 days.

(21) Appl. No.: 11/834,540

(22) Filed: Aug. 6, 2007

(65) Prior Publication Data
US 2008/0033450 A1 Feb. 7, 2008

Related U.S. Application Data

(60) Provisional application No. 60/835,543, filed on Aug. 4, 2006.

(51) Int. Cl.
*A61B 1/04* (2006.01)

(52) U.S. Cl. ........ 600/129; 600/107; 600/114; 600/130; 600/173; 600/204; 604/264; 604/506; 606/108

(58) Field of Classification Search .................. 600/114, 600/173, 202–205, 223, 245–246, 121–125, 600/106–107, 151–156; 604/158–165.01, 604/264–284, 506–513
See application file for complete search history.

(56) References Cited

U.S. PATENT DOCUMENTS

| 3,610,231 A | 10/1971 | Takahashi et al. |
| 3,643,653 A | 2/1972 | Takahashi et al. |
| 3,739,770 A | 6/1973 | Mori |
| 3,897,775 A | 8/1975 | Furihata |
| 4,261,344 A | 4/1981 | Moore et al. |
| 4,573,450 A | 3/1986 | Arakawa |
| 4,586,491 A | 5/1986 | Carpenter |
| 4,625,236 A | 11/1986 | Fujimori et al. |
| 4,646,722 A | 3/1987 | Silverstein et al. |
| 4,721,097 A | 1/1988 | D'Amelio |

(Continued)

FOREIGN PATENT DOCUMENTS

CN 1 628 603 6/2005

(Continued)

OTHER PUBLICATIONS

International Search Report for PCT/US2008/069435, filed Jul. 8, 2008, mailed Oct. 23, 2008, 8 pgs.

(Continued)

*Primary Examiner* — Matthew J Kasztejna
(74) *Attorney, Agent, or Firm* — Schwegman, Lundberg & Woessner, P.A.

(57) ABSTRACT

Disclosed is a disposable access port for use in endoscopic procedures, including laparoscopic procedures. The access port includes a cannula with an embedded camera in communication with an external control box. In operation, a trocar is combined with the access port to facilitate insertion of the access port into an anatomical site. Prior to insertion, the camera is pushed inside the cannula, where it remains during insertion. The trocar is removed after the access port has been inserted to allow surgical instruments to access the anatomical site. During removal of the trocar, a portion of the trocar urges the camera out of the cannula, thereby allowing visualization of the anatomical site. The camera can be fixedly or adjustably mounted on the port. A camera may also be mounted on the trocar. The trocar may include irrigation and suction channels to facilitate a clear view of the anatomical site.

24 Claims, 19 Drawing Sheets

U.S. PATENT DOCUMENTS

| | | | |
|---|---|---|---|
| 4,741,326 | A | 5/1988 | Sidall et al. |
| 4,800,870 | A | 1/1989 | Reid, Jr. |
| 4,825,850 | A | 5/1989 | Opie et al. |
| 4,852,551 | A | 8/1989 | Opie et al. |
| 4,869,238 | A | 9/1989 | Opie et al. |
| 4,870,488 | A | 9/1989 | Ikuno et al. |
| 4,873,965 | A | 10/1989 | Danieli |
| 4,899,732 | A | 2/1990 | Cohen |
| 4,905,667 | A | 3/1990 | Foerster et al. |
| 4,907,395 | A | 3/1990 | Opie et al. |
| 4,911,564 | A | 3/1990 | Baker |
| 4,947,827 | A | 8/1990 | Opie et al. |
| 4,979,496 | A | 12/1990 | Komi |
| 4,991,565 | A | 2/1991 | Takahashi et al. |
| 5,019,040 | A | 5/1991 | Itaoka et al. |
| 5,025,778 | A | 6/1991 | Silverstein et al. |
| 5,050,585 | A | 9/1991 | Takahashi |
| RE34,110 | E | 10/1992 | Opie et al. |
| 5,166,787 | A | 11/1992 | Irion |
| 5,178,130 | A | 1/1993 | Kaiya |
| 5,193,525 | A | 3/1993 | Silverstein et al. |
| 5,271,381 | A | 12/1993 | Ailinger et al. |
| 5,305,121 | A * | 4/1994 | Moll ............................... 348/45 |
| 5,329,887 | A | 7/1994 | Ailinger et al. |
| 5,337,734 | A | 8/1994 | Saab |
| 5,443,781 | A | 8/1995 | Saab |
| 5,447,148 | A | 9/1995 | Oneda et al. |
| 5,483,951 | A | 1/1996 | Frassica et al. |
| 5,518,501 | A | 5/1996 | Oneda et al. |
| 5,520,607 | A | 5/1996 | Frassica et al. |
| 5,533,496 | A | 7/1996 | De Faria-Correa et al. |
| 5,536,236 | A | 7/1996 | Yabe et al. |
| 5,626,553 | A | 5/1997 | Frassica et al. |
| 5,667,476 | A | 9/1997 | Frassica et al. |
| 5,679,216 | A | 10/1997 | Takayama et al. |
| 5,685,822 | A | 11/1997 | Harhen |
| 5,692,729 | A | 12/1997 | Harhen |
| 5,702,348 | A | 12/1997 | Harhen |
| 5,722,933 | A | 3/1998 | Yabe et al. |
| 5,752,912 | A | 5/1998 | Takahashi et al. |
| 5,762,603 | A | 6/1998 | Thompson |
| 5,817,061 | A * | 10/1998 | Goodwin et al. ........ 604/164.03 |
| 5,827,177 | A | 10/1998 | Oneda et al. |
| 5,860,914 | A | 1/1999 | Chiba et al. |
| 5,876,329 | A | 3/1999 | Harhen |
| 5,916,147 | A | 6/1999 | Boury |
| 5,924,977 | A | 7/1999 | Yabe et al. |
| 5,989,182 | A | 11/1999 | Hori et al. |
| 5,989,224 | A * | 11/1999 | Exline et al. ............. 604/167.02 |
| 6,017,358 | A | 1/2000 | Yoon |
| 6,066,090 | A | 5/2000 | Yoon |
| 6,099,464 | A | 8/2000 | Shimizu et al. |
| 6,099,485 | A | 8/2000 | Patterson |
| 6,174,280 | B1 | 1/2001 | Oneda et al. |
| 6,190,330 | B1 | 2/2001 | Harhen |
| 6,214,028 | B1 | 4/2001 | Yoon et al. |
| 6,261,226 | B1 | 7/2001 | McKenna et al. |
| 6,261,307 | B1 | 7/2001 | Yoon et al. |
| 6,277,064 | B1 | 8/2001 | Yoon |
| 6,350,231 | B1 | 2/2002 | Ailinger et al. |
| 6,387,043 | B1 * | 5/2002 | Yoon ............................ 600/109 |
| 6,461,294 | B1 | 10/2002 | Oneda et al. |
| 6,527,704 | B1 * | 3/2003 | Chang et al. ................. 600/112 |
| 6,547,724 | B1 | 4/2003 | Soble et al. |
| 6,648,816 | B2 * | 11/2003 | Irion et al. ................... 600/173 |
| 6,736,773 | B2 | 5/2004 | Wendlandt et al. |
| 6,748,975 | B2 | 6/2004 | Hartshorne et al. |
| 6,845,190 | B1 | 1/2005 | Smithwick et al. |
| 6,974,411 | B2 | 12/2005 | Belson |
| 7,004,900 | B2 | 2/2006 | Wendlandt et al. |
| 7,029,435 | B2 * | 4/2006 | Nakao .......................... 600/153 |
| 7,041,050 | B1 * | 5/2006 | Ronald ......................... 600/104 |
| 2002/0039400 | A1 | 4/2002 | Kaufman et al. |
| 2002/0156347 | A1 | 10/2002 | Kim et al. |
| 2002/0193662 | A1 | 12/2002 | Belson |
| 2003/0004399 | A1 | 1/2003 | Belson |
| 2003/0032863 | A1 | 2/2003 | Kazakevich |
| 2003/0040668 | A1 | 2/2003 | Kaneko et al. |
| 2003/0065250 | A1 | 4/2003 | Chiel et al. |
| 2003/0088152 | A1 | 5/2003 | Takada |
| 2003/0093031 | A1 | 5/2003 | Long et al. |
| 2003/0093088 | A1 | 5/2003 | Long et al. |
| 2003/0105386 | A1 | 6/2003 | Voloshin et al. |
| 2003/0120130 | A1 | 6/2003 | Glukhovsky |
| 2003/0125788 | A1 | 7/2003 | Long |
| 2003/0153866 | A1 | 8/2003 | Long et al. |
| 2003/0171650 | A1 | 9/2003 | Tartaglia et al. |
| 2003/0187326 | A1 | 10/2003 | Chang |
| 2003/0195545 | A1 | 10/2003 | Hermann et al. |
| 2003/0225433 | A1 | 12/2003 | Nakao |
| 2003/0233115 | A1 | 12/2003 | Eversull et al. |
| 2004/0034278 | A1 | 2/2004 | Adams |
| 2004/0049096 | A1 | 3/2004 | Adams |
| 2004/0059191 | A1 | 3/2004 | Krupa et al. |
| 2004/0080613 | A1 | 4/2004 | Moriyama |
| 2004/0111019 | A1 | 6/2004 | Long |
| 2004/0141054 | A1 | 7/2004 | Mochida et al. |
| 2005/0010084 | A1 | 1/2005 | Tsai |
| 2005/0038317 | A1 | 2/2005 | Ratnakar |
| 2005/0085693 | A1 | 4/2005 | Belson et al. |
| 2005/0085790 | A1 | 4/2005 | Guest et al. |
| 2005/0096502 | A1 * | 5/2005 | Khalili ......................... 600/106 |
| 2005/0165272 | A1 | 7/2005 | Okada et al. |
| 2005/0228224 | A1 | 10/2005 | Okada et al. |
| 2005/0272975 | A1 | 12/2005 | McWeeney et al. |
| 2005/0272977 | A1 | 12/2005 | Saadat et al. |
| 2006/0106286 | A1 | 5/2006 | Wendlandt et al. |
| 2006/0149129 | A1 | 7/2006 | Watts et al. |
| 2006/0183975 | A1 | 8/2006 | Saadat et al. |
| 2006/0293562 | A1 | 12/2006 | Uchimura et al. |
| 2009/0036739 | A1 * | 2/2009 | Hadani ......................... 600/121 |

FOREIGN PATENT DOCUMENTS

| | | |
|---|---|---|
| DE | 196 26433 | 1/1998 |
| EP | 0 586 162 | 3/1994 |
| WO | WO 93/15648 | 8/1993 |
| WO | WO 02/085194 | 10/2002 |

OTHER PUBLICATIONS

Invitation to Pay Additional Fees for PCT/US2008/071390, filed Jul. 28, 2008, mailed Nov. 11, 2008, 5 pgs.
U.S. Appl. No. 11/153,007, filed Jun. 14, 2005, Seddiqui et al.
U.S. Appl. No. 11/160,646, filed Jul. 1, 2005, Desai et al.
U.S. Appl. No. 11/215,660, filed Aug. 29, 2005, Watts et al.
U.S. Appl. No. 11//609,838, filed Dec. 12, 2006, Bayer et al.
U.S. Appl. No. 11/626,189, filed Jan. 23, 2007, Bayer et al.
U.S. Appl. No. 11/673,470, filed Feb. 9, 2007, Bayer et al.
U.S. Appl. No. 11/672,020, filed Feb. 6, 2007, Bayer et al.
U.S. Appl. No. 11/736,438, filed Apr. 17, 2007, Bayer.
U.S. Appl. No. 11/751,596, filed May 21, 2007, Bayer.
U.S. Appl. No. 11/751,597, filed May 21, 2007, Bayer et al.
U.S. Appl. No. 11/751,605, filed May 21, 2007, Diel et al.
U.S. Appl. No. 11/828,835, filed Jul. 26, 2007, Bayer.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
Invitation to Pay Additional Fees for PCT/US2007/002096, filed Jan. 23, 2007, mailed Jul. 6, 2007, 4 pgs.
Invitation to Pay Additional Fees for PCT/US2007/003631, filed Feb. 9, 2007, mailed Aug. 7, 2007, 5 pgs.
Invitation to Pay Additional Fees for PCT/US2007/003322, filed Feb. 6, 2007, mailed Aug. 7, 2007, 6 pgs.

* cited by examiner

SURGICAL PORT WITH EMBEDDED IMAGING DEVICE

This application claims the benefit of U.S. Provisional Application No. 60/835,543, filed Aug. 4, 2006, the entire contents of which are incorporated by reference.

BACKGROUND OF THE INVENTION

1. Field of the Invention

The present invention relates generally to the field of endoscopic devices, and more particularly, to laparoscopic surgical devices including laparoscopic ports which provide minimally invasive access to the abdominal cavity.

2. Description of the State of the Art

Endoscopic surgery has become the new standard for surgical procedures. A specific type of endoscopic surgery, laparoscopic surgery, has become the preferred method for surgeries involving the organs within an abdominal cavity or peritoneal cavity of a patient.

Laparoscopic surgery employs small incisions appropriately placed on a patient's abdomen instead of one large incision as was the custom in traditional laparotomies or "open" surgeries. Instruments are inserted through these small incisions, and the surgery is performed via the manipulation of these instruments.

Laparoscopic ports are employed to provide effective access to the abdominal cavity. Such ports maintain an airproof seal and to facilitate the insertion of medical devices into the incisions. Multiple incisions and multiple laparoscopic ports allow the simultaneous use of different instruments including a laparoscope, which displays images on a video display in order to guide the surgeon. The port through which the laparoscope is inserted is commonly referred to as the primary port, while ports for the other instruments are referred to as ancillary ports.

Many laparoscopic ports, also known as laparoscopic access systems, involve a cannula, which is a hollow tube, and a removable trocar, which is inserted through the cannula to facilitate insertion of the cannula through the abdominal wall. The distal tip of a trocar may be either sharp or blunt. The external opening of the cannula through which instruments are inserted is often referred to as the entry port of the cannula and the opening at the tip of the cannula through which the instrument emerges inside the peritoneal cavity is referred to as the exit port.

One of the first steps during a laparoscopic surgical procedure involves insufflation of the abdomen with nitrogen or carbon dioxide gas. The resulting expansion of the abdomen reduces the risk of injury to the contents of the abdomen during subsequent insertion of the ports and also allows the surgeons more freedom and space to manipulate instruments and perform the surgery.

Insertion of the primary port is accomplished either blindly or through the use of a device that allows some visualization through the laparoscope's camera as the tip of the trocar penetrates the abdominal wall. Insertion of the ancillary ports is generally accomplished while using a laparoscope at the primary port to observe the peritoneum at the ancillary point of insertion. Such observation reduces the risk of damaging abdominal organs beneath the point of insertion, such as may occur when the trocar is pushed to far into the abdominal cavity.

Laparoscopic surgery is generally performed with only one source of visualization, namely, the camera at the tip of the laparoscope. However, in order to minimize risk of injury to the patient, it is preferable to observe the exit ports of all cannulas every time an instrument is inserted or withdrawn. Such observation currently requires that the camera on the tip of the laparoscope be directed toward a particular port. This would then result in the loss of visualization of the surgical field, which interrupts the surgical procedure and interrupts the use of the surgical instruments until the surgical field can again be visualized with the laparoscope.

In addition, sometimes during the course of a surgery an endoscopist or surgeon determines that the view through the laparoscope is not optimal for safe manipulation of the instruments, and it is necessary to withdraw the laparoscope from the primary port and insert it through one of the ancillary ports in order to provide visualization of the surgical field from a more appropriate angle. This also interrupts the surgical procedure and increases risk to the patient.

Therefore, it is desirable to have multiple concurrent views of the surgical field. With currently available technology, the only way to provide such visualization would be through the insertion of a second laparoscope. However, because laparoscopes are relatively long and heavy, a surgeon or an assistant must have one hand occupied with the laparoscope at all times unless it is attached to a robotic arm. Furthermore, laparoscopes require sterilization between uses, and using more than one laparoscope for a procedure would result in significant additional expense for sterilization. Additionally, because many laparoscopes have cameras with a nonadjustable viewing angle, multiple laparoscopes, each having a different viewing angle, are often required to be exchanged during a surgical procedure. Because laparoscopes are very expensive, using more than one laparoscope for a surgical procedure would require a hospital or surgical facility to make a substantial additional investment to have extra laparoscopes on hand, which also requires increases maintenance and sterilization expenses.

Therefore, there exists a need for a more practical and less expensive method of providing multiple concurrent views of a surgical field. There is also a need for a more efficient method of viewing the insertion point of ancillary ports through the peritoneum and of viewing insertion and withdrawal of surgical instruments at the ancillary ports. Further, there exists a need to reduce manipulation and exchange of laparoscopes and other endoscopic instruments during minimally invasive procedures, which would reduce the time required to complete the procedure, limit the overall cost, and reduce patient risk. The present invention satisfies these and other needs.

SUMMARY OF THE INVENTION

Briefly and in general terms, the present invention is directed to surgical endoscopic ports, including laparoscopic ports. An endoscopic port assembly comprises an endoscopic port including a lumen, a trocar sized to be insertable into the lumen, and an imaging device disposed on either one of the endoscopic port and the trocar.

The port of endoscopic port assembly, in other aspects of the present invention, further includes a handle at a proximal end of the port and a cannula at a distal end of the port, the imaging device being disposed on the cannula. In other aspects, the imaging device is mounted on the cannula and is movable between a radially inward position and a radially outward position.

In detailed aspects, the imaging device includes either one or both of an imaging sensor and a light source. In other aspects, the imaging device includes an imaging lens that is inside the cannula when the imaging device is in the inward position and is outside the cannula when the imaging device is in the outward position.

The endoscopic port assembly, in other aspects of the present invention, further comprises a detent mechanism that holds the imaging device in the outward position until the imaging device is pushed toward the inward position. In other aspects, the assembly further comprises a movable control member that is connected to the imaging device such that manipulation of the control member moves the imaging device.

In detailed aspects, a portion of the lumen is defined by a tubular wall to which the imaging device is movably mounted. The trocar includes a shaft. There is a gap between the shaft and the tubular wall when the trocar is inserted into the lumen. The gap sized to receive at least a portion of the imaging device.

The trocar, in other aspects of the invention, includes a distal tip region connected to the shaft, the distal tip region being wider than the shaft such that, when the trocar is removed from the port, the distal tip region pushes the portion of the imaging device disposed within the gap such that the imaging device moves in a radially outward direction from the tubular wall.

In yet other aspects of the invention, the imaging device is attached to the trocar such that the imaging device extends beyond the distal end of the port when the trocar is inserted into the lumen.

The endoscopic port assembly, in further aspects of the invention, comprises a controller in communication with the imaging device, the controller providing power and control commands to the imaging device, the controller receiving image signals from the imaging device. In other aspects, the controller and the imaging device each include a wireless transceiver.

In other aspects of the invention, a laparoscopic device comprises a laparoscopic port including an imaging device. In detailed aspects, the port includes a handle and a cannula connected to the handle, the handle having an instrument entry opening in communication with an instrument exit opening at a distal tip of the cannula. In other detailed aspects, the imaging device includes an imaging lens and is mounted to the cannula such that the lens is movable between a position outside the cannula and a position inside the cannula. In other aspects, the imaging device includes an imaging lens disposed at a distal edge of the cannula.

The cannula of the laparoscopic device, in other aspects of the invention, defines at least a portion of an instrument passageway extending from the instrument entry port to the instrument exit port. In other aspects, the cannula includes a lumen housing the imaging device. In yet other aspects, the cannula includes a lumen capable of provide irrigation, suction, or both.

In other aspects of the invention, an endoscopic port assembly comprises an endoscopic port including a proximal end, a distal end, an instrument passageway extending from the proximal and distal ends, and a first seal disposed within the passageway, the first seal movable between an open position at which air may flow through the passageway and a closed position at which air flow through the passageway from the distal end to the proximal end is blocked. The assembly also comprises an imaging device disposed on the port.

In detailed aspects, the first seal is adapted to move to the open position when an instrument is inserted into the passageway and to move to the closed position when the instrument is removed from the passageway.

The port of the endoscopic port assembly, in further aspects of the invention, further includes a second seal adapted to block air flow through the passageway when an instrument is inserted into the passageway. In other aspects, a portion of the passageway is defined by a tubular wall to which the imaging device is mounted. In yet other aspects, the imaging device includes a lens and is movably mounted to allow the lens to be adjustably oriented at an angle between about zero degrees and about ninety degrees from a central axis of the tubular wall. In further aspects, the imaging device includes a lens located at a distal edge of the tubular wall.

In other aspects of the present invention, a method of deploying an endoscopic viewing device comprises inserting a trocar into an endoscopic port that includes an imaging device oriented in an outward position. The method also comprises pushing the imaging device from the outward position to an inward position after the trocar is inserted in the port. The method further comprises removing the trocar from the port such that the imaging device is urged from the inward position to the outward position.

In further aspects of the invention, the method comprises pushing the imaging device from the outward position to the inward position after the trocar is removed from the port, the imaging device being pushed by an abdominal wall.

In detailed aspects, when the imaging device is in the outward position, the imaging device protrudes outwardly from an exterior surface of the port. In other detailed aspects, when the imaging device is in the inward position, the imaging device does not protrude outwardly from an exterior surface of the port or protrudes less than when the imaging device is in the outward position.

The features and advantages of the invention will be more readily understood from the following detailed description which should be read in conjunction with the accompanying drawings.

DETAILED DESCRIPTION OF THE INVENTION

The term "endoscopic surgery" is a broad term that includes many varieties of surgeries such as laparoscopy. The scope of the present invention includes various types of endoscopic procedures, including laparoscopic surgery and other minimally invasive forms of surgery. The present invention also applies to any type of surgery that makes use of a trocar or cannula or similar devices.

In an embodiment of the present invention, a trocar is inserted into a cannula until it snaps into place as the projections on the trocar handle engage with complimentary grooves on the corresponding sections of the cannula handle.

An integrated imaging device, such as a camera, forms part of the cannula, trocar, or both. Corresponding electrical cabling for the camera is connected to connectors on an external control box and the cannula handle. The camera is powered on through the control box, and the control box begins to process the images captured by the camera and displays them on a monitor.

The camera is housed in a camera capsule. In some embodiments, the camera capsule forms part of the cannula and is initially located outside the main lumen of the cannula adjacent to the shaft of the trocar. In use, the camera capsule is tucked by hand into the main lumen prior to inserting the trocar and cannula through the abdominal wall or other anatomical site. Once the trocar and cannula have been inserted into the anatomical site, the trocar is withdrawn from the cannula, which in turn causes the camera capsule to be swiveled into its outside lumen position. Other instruments can now be inserted through the lumen of the cannula as images are collected by the integrated camera. Other instruments include those used for cutting, ablation, suction, irrigation, grasping, retracting, and suturing.

After the surgery is completed, the cannula is simply withdrawn from anatomical site, causing the camera capsule to be automatically swiveled into its inside lumen position due to pressure and friction from tissue surrounding the cannula. The cannula is disconnected from the electrical cabling and the control box and is disposed along with the trocar.

Figure 1:
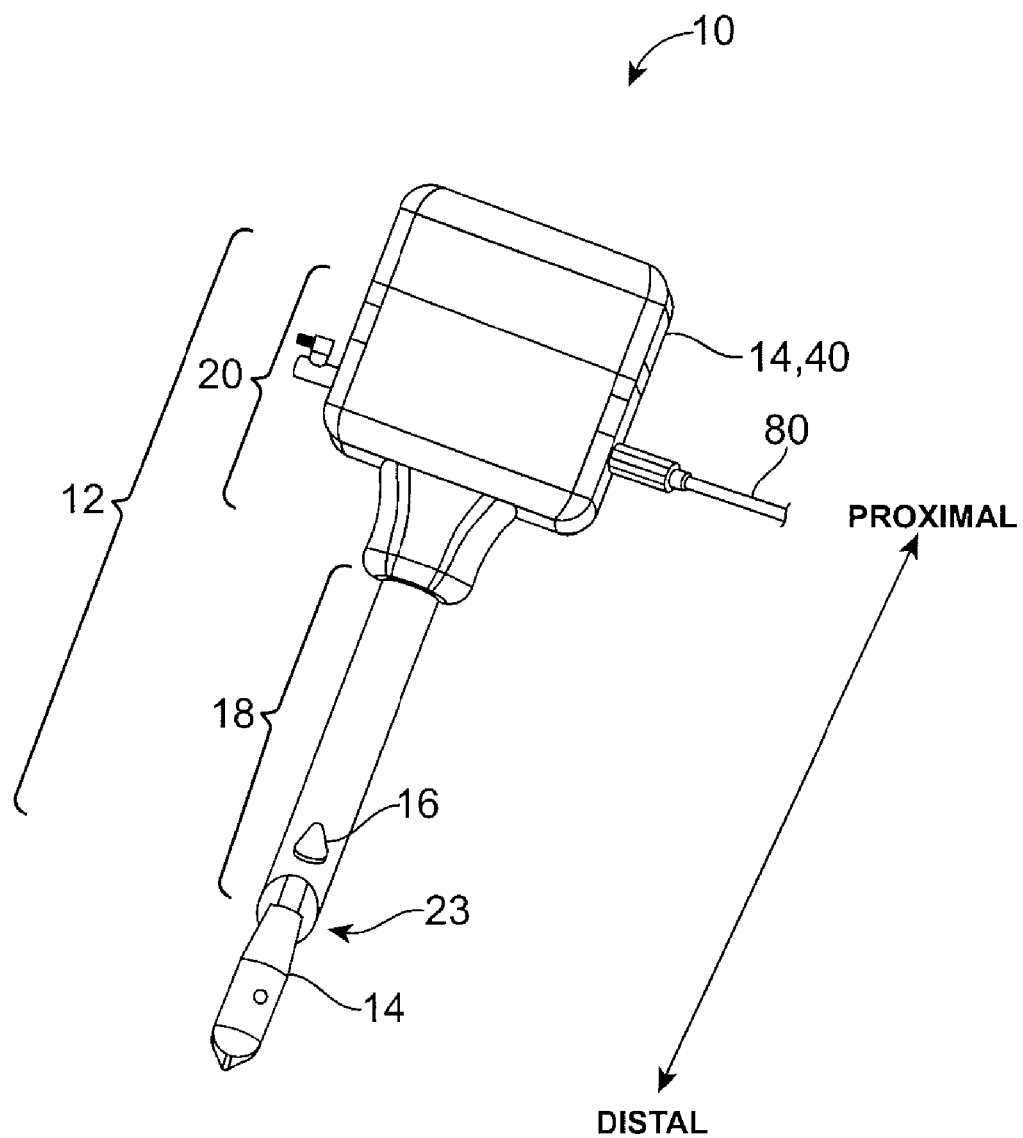
FIG. 1 is a perspective view of a surgical access port assembly showing an access port including a cannula, a camera embedded in the cannula, and a trocar inserted into the cannula such that the a trocar tip extends beyond a cannula tip.

Referring now in more detail to the exemplary drawings for purposes of illustrating embodiments of the invention, wherein like reference numerals designate corresponding or like elements among the several views, there is shown in FIG. 1 a laparoscopic port 10 comprising two main mechanical units: a cannula 12 and a trocar 14. The laparoscopic port 10 is optionally connected by means of a cable 80 to a control box 74 shown in FIG. 2. Although the assembly illustrated in FIG. 1 is described as a laparoscopic port, it will be appreciated that the illustrated assembly may also be used for providing surgical access to various anatomical cavities and regions in addition to the abdominal cavity of a patient.

Figure 3:
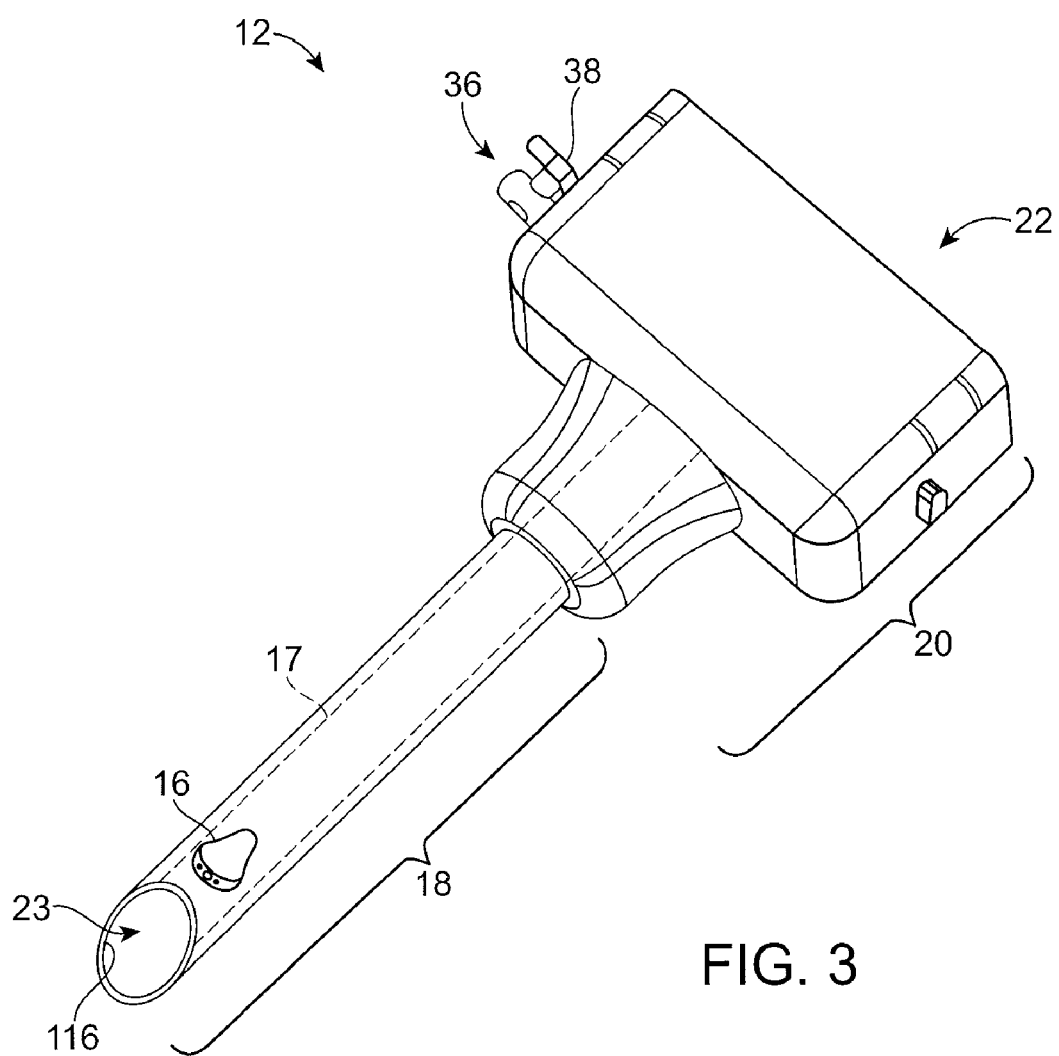
FIG. 3 is a front perspective view of the cannula showing an elongate sleeve connected to a cannula handle and an instrument exit opening formed in the sleeve.

FIG. 3 shows the cannula 12 separated from the trocar 14. The cannula 12 includes an integrated, embedded camera 16 capable of providing a view of the portion of the peritoneal cavity that lies distal to the exit port of the cannula. The cannula 12 includes a single lumen 17, or interior passageway, that provides access to the abdominal cavity for the insertion of surgical instruments. A portion of the lumen 17 is defined by an tubular member or elongate sleeve 18 which contains the camera 16. The sleeve 18 extends from a cannula handle 20 on a proximal end 22 of the cannula 12. At the distal end of the sleeve 18, there is an exit port 23 in the form of a circular opening through which surgical instruments enter the abdominal cavity of a patient.

The cannula 12 can be constructed from multiple parts of plastic, such as polyethylene, which are fastened together by a method, such as snap-fit, welding, or adhesive bonding, that ensures an air-tight seal to separate compartments within the cannula from the outside environment.

Figure 4:
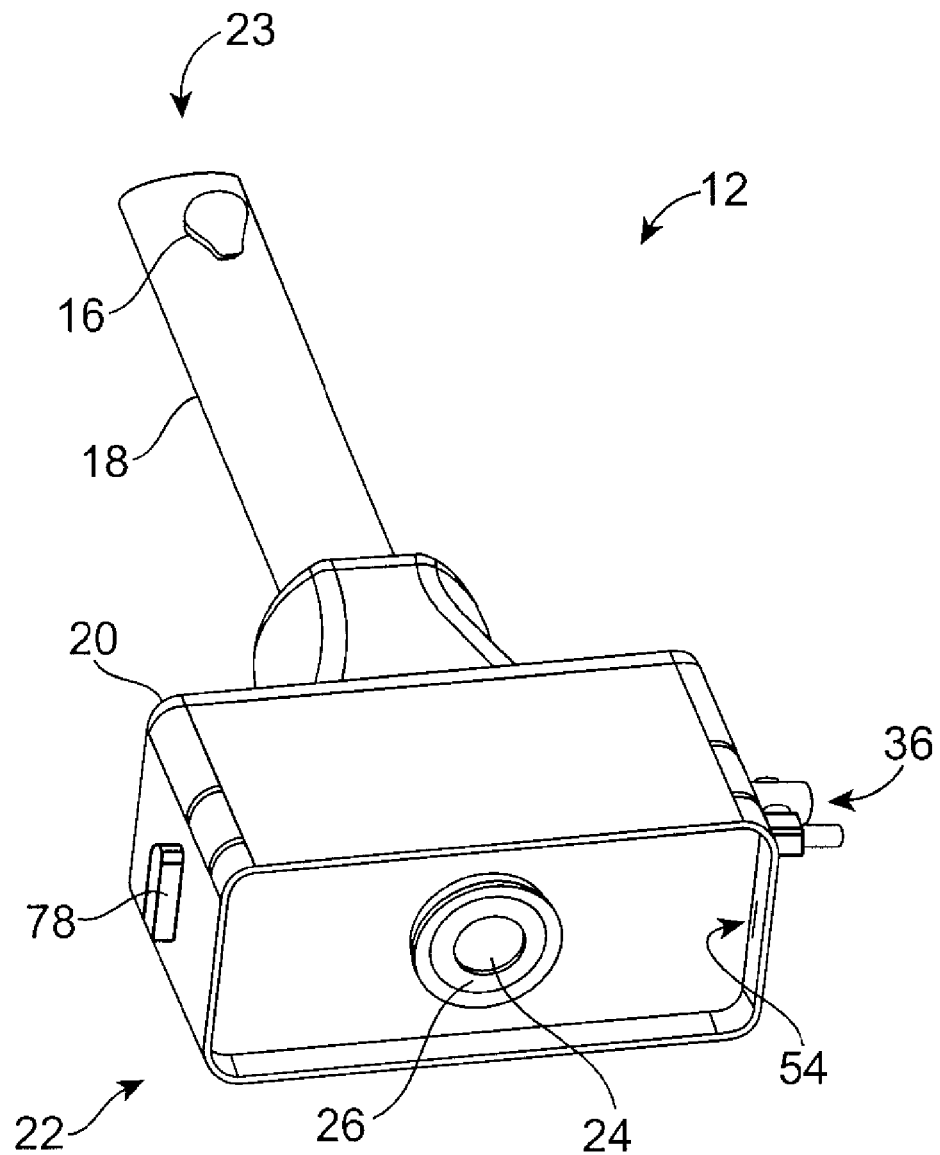
FIG. 4 is a rear perspective view of the cannula showing an instrument entry opening formed in the cannula handle and a concentric seal adjacent the entry opening.

Referring now to FIG. 4, the cannula handle 20 includes an entry port 24 in the form of a circular opening that provides proximal access to the lumen of the cannula. In order to maintain insufflation pressure within the abdominal cavity, a concentric seal 26 adjacent the entry port 24 is configured to prevent leakage of gas when an instrument is present within the cannula 12. The concentric seal 26 can be made from a flexible material such as rubber.

Figure 5:
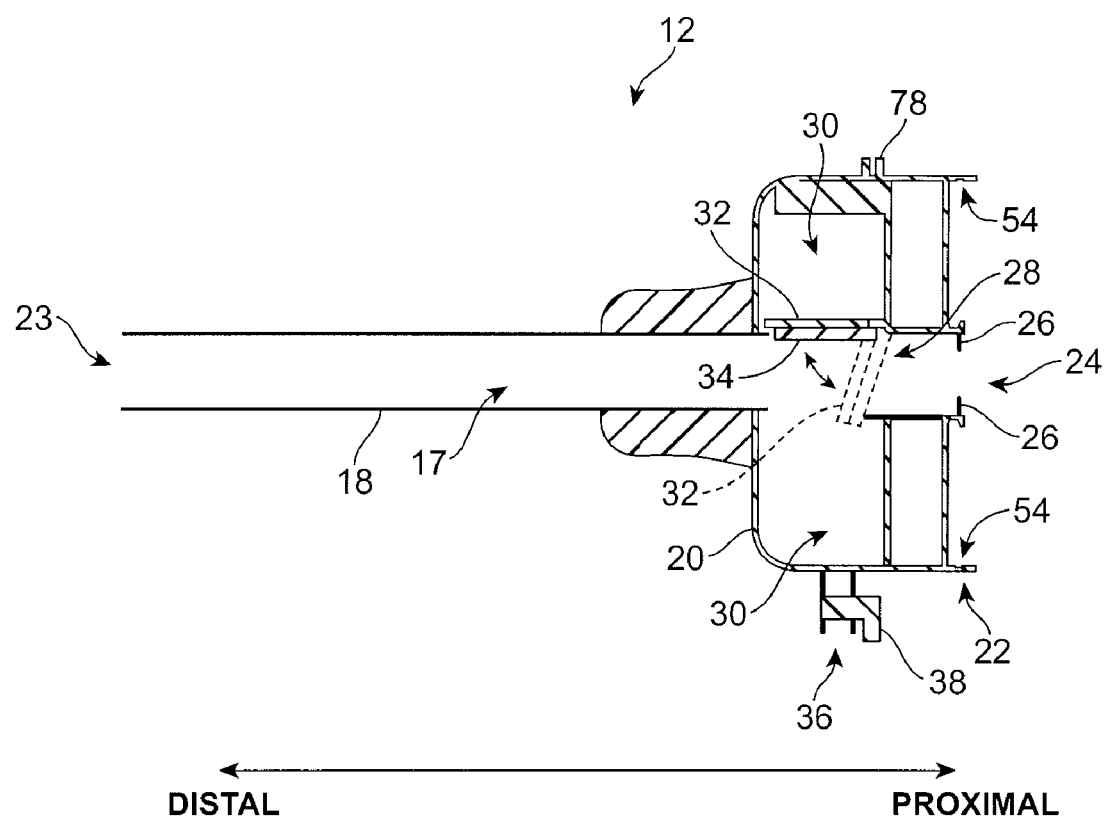
FIG. 5 is a cross-sectional view of the cannula showing an instrument passageway extending from the instrument entry opening to the instrument exit opening, and another seal disposed within the instrument passageway between the concentric seal and the instrument exit opening.

As shown in FIG. 5, in the cannula handle 20 there is an interior seal 28 in the form of a hatch that provides instrument access to an airtight compartment 30 and the sleeve 18. A hinged door 32 includes a lip 34. The door 32 is shown in an open position (illustrated in solid lines) and in a closed position (illustrated in broken lines). When in the closed position, the door 32 and lip 34 ensures an air tight seal. The interior seal 28 maintains insufflation pressure within the abdominal cavity when an instrument is not present in the cannula. The hinged door 32 is designed to open toward the distal end of the cannula when an instrument is inserted into the cannula 12 from the entry port 24 at the proximal end 22. The hinged door 32 can be constructed from plastic, while the lip 34 can be formed from a deformable material such as rubber.

Still referring to FIG. 5, on one side of the cannula handle 20 there is an insufflation air port 36. During a laparoscopic procedure, the air port 36 allows nitrogen, carbon dioxide, or other gas to be introduced into a patient's abdominal cavity to achieve and maintain a desired insufflation pressure. A lever 38 controls whether a valve inside the air port 36 is open or closed.

Figure 6:
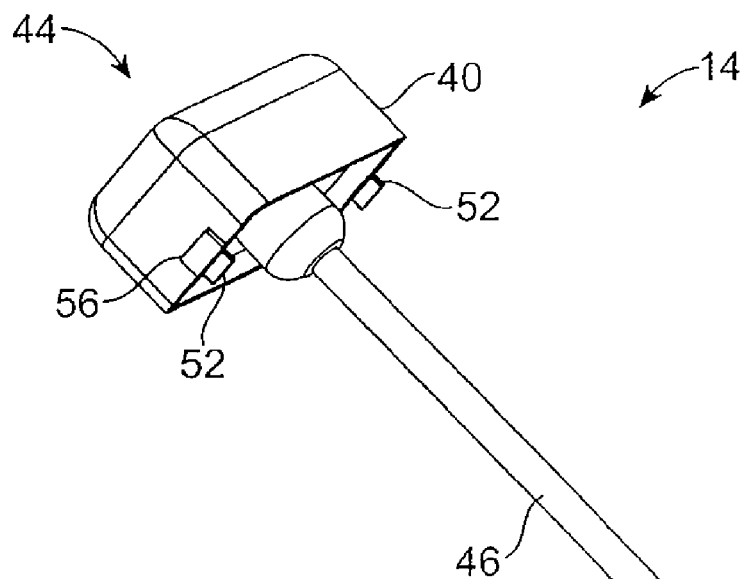
FIG. 6 is a perspective view of the trocar showing a trocar shaft connected to a trocar handle, the trocar shaft having a medial segment and distal segment wider than the medial segment.
Figure 6:
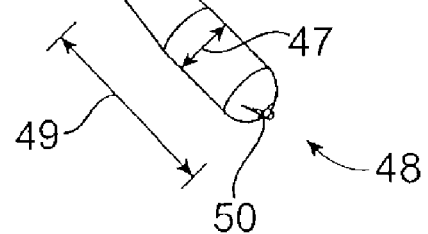

FIG. 6 shows the trocar 14 separated from the cannula 12. The trocar 14 can be constructed from components made from a plastic such as polyurethane, which are joined together by a method such as snap-fit. Components of the trocar 14 can also be constructed of a metal. The trocar 14 includes a trocar handle 40 at its proximal end 44. A narrow cylindrical member or shaft 46 extends from the trocar handle 40 to a distal end 48 of the trocar 14. The shaft 46 has a greater diameter 47 along a short distance 49 at the distal end 48. At the very tip of the shaft 46, there may be a sharp point 50 to facilitate insertion of the trocar and cannula through the abdominal wall or other anatomical region.

Figure 7:
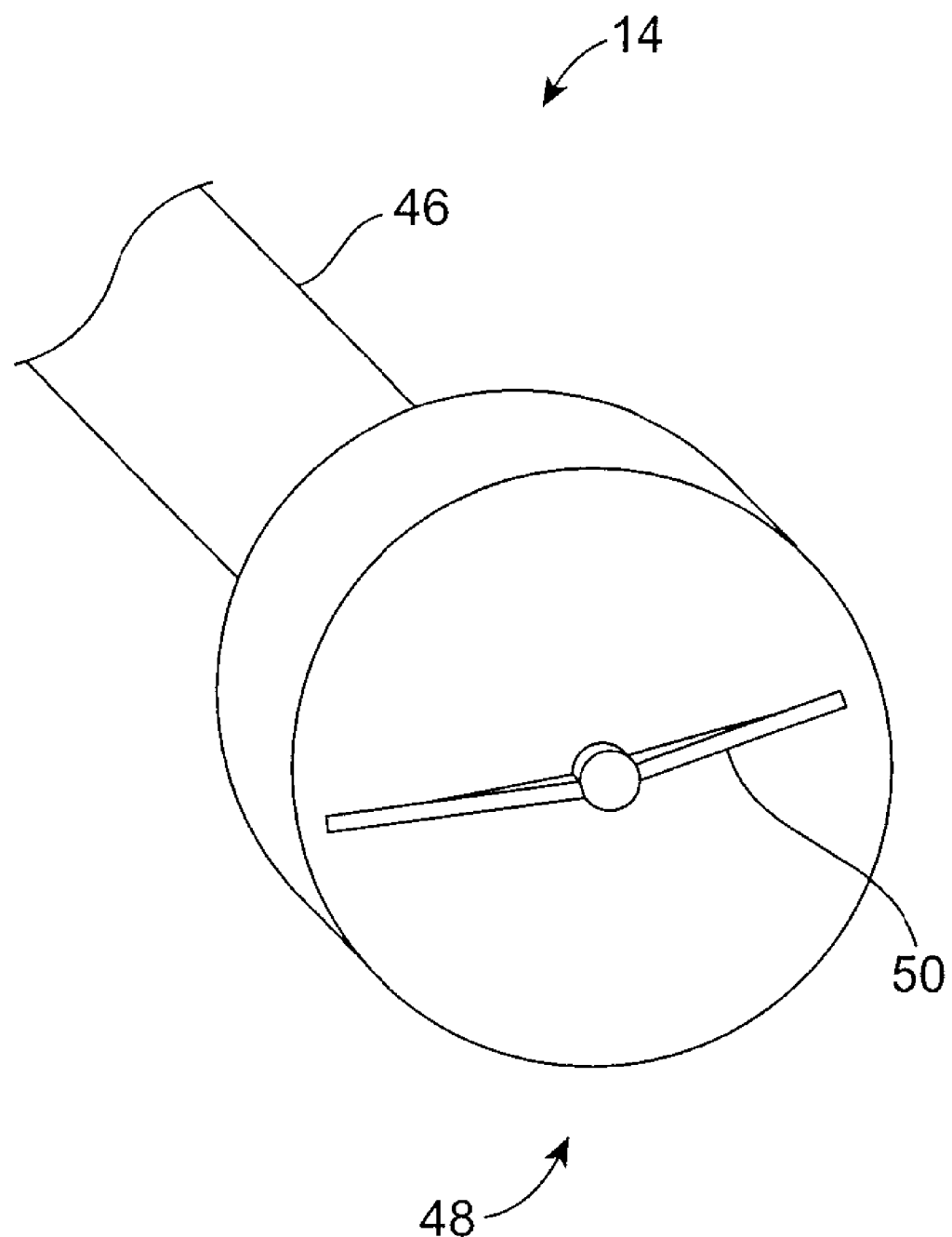
FIG. 7 is a close-up perspective view of the trocar shaft showing a sharp point on the distal segment.

As illustrated in FIGS. 6 and 7, the point 50 at the very tip 48 of the trocar shaft 46 may be shaped like a triangle.

Referring again to FIG. 6, the trocar handle 40 includes two projection features 52, one on each side. The projection features 52 mate with complimentary grooves 54 (FIG. 5) on the corresponding sections of a cannula handle 20. Each projection feature 52 is attached to a depressible button 56 which facilitates release of the trocar handle 40 from the cannula handle 20.

Figure 8:
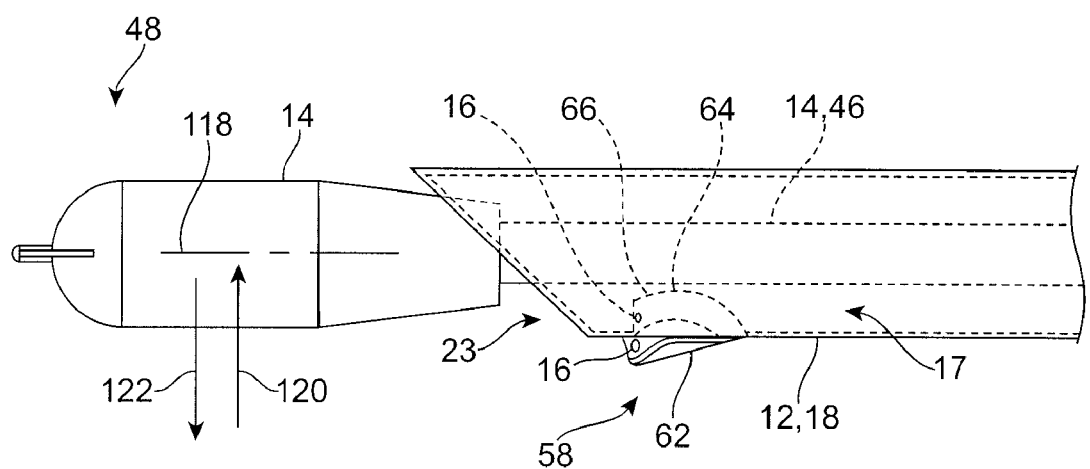
FIG. 8 is a close-up view side view of a distal region of the access port showing a gap between the medial portion of the trocar and an inner surface of the trocar sleeve, the gap sized to receive the embedded camera which is movable between a radially inward position and a radially outward position.

As shown in FIG. 8, the camera 16 and one or more light sources are integrated into an adjustable imaging device or camera capsule 58 located at a distal portion of a cannula 12. The camera capsule 58 is shown in a position outside the cannula lumen 17 (illustrated with solid lines) and in a position inside the cannula lumen 17 (illustrated with broken lines). A trocar 14 is shown inserted into the cannula 12.

Figure 9:
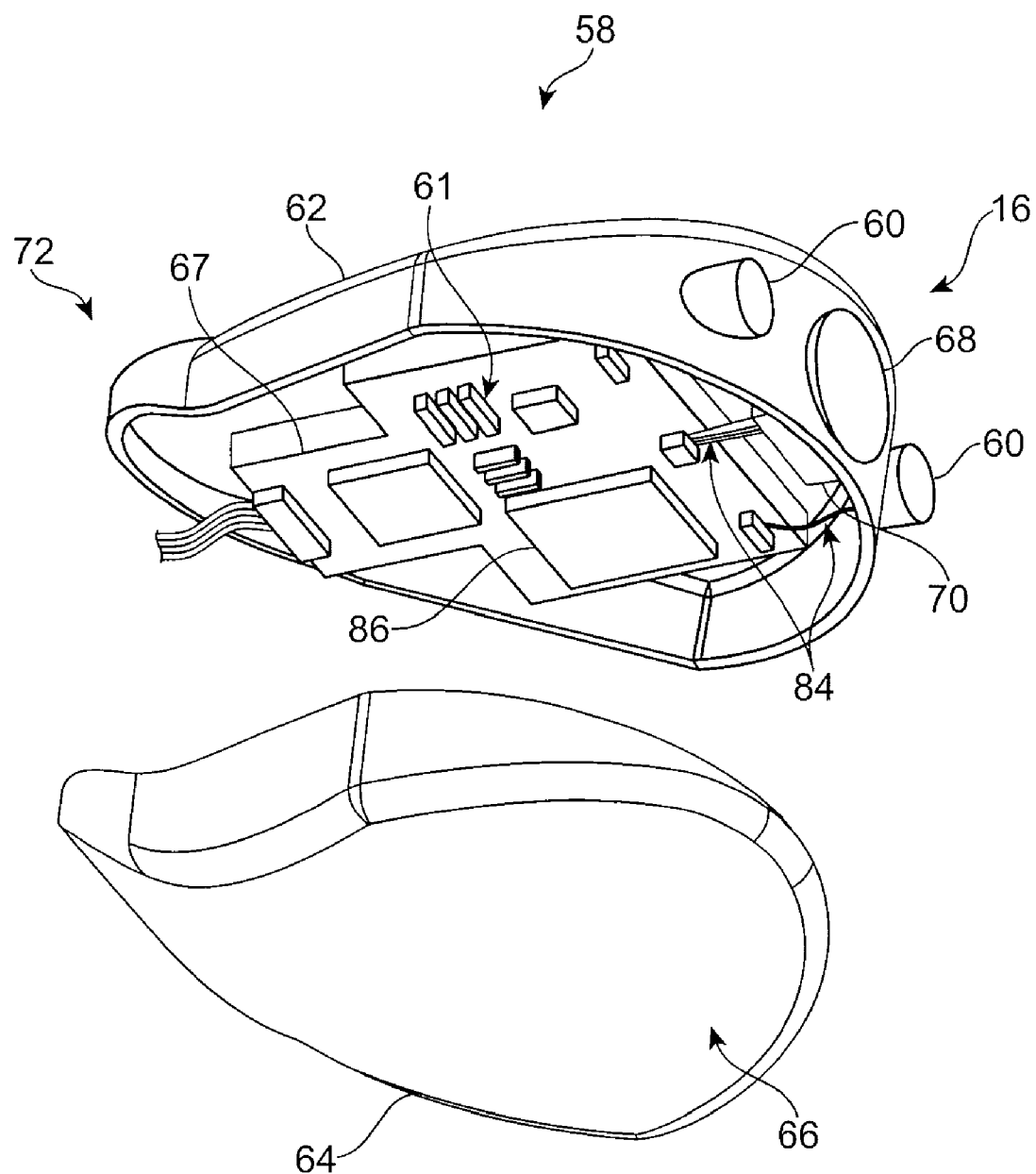
FIG. 9 is an exploded view of a camera capsule showing light sources, the camera, and associated electronics housed within an upper housing and a bottom housing with a distally facing sloped surface that allows the trocar to push the camera to the radially outward position when the trocar is withdrawn from the cannula.

As shown in FIG. 9, the camera capsule 58 includes the camera 16 and associated electronics 61. The capsule is created from two complementary housing components 62, 64 which can be constructed from a plastic such as polyethylene. The bottom housing 64 exhibits a decline shape or distally facing sloped surface 66, which allows the retraction of a trocar from a cannula to push the camera capsule 58 from a position inside the cannula lumen to a position outside the cannula lumen. A single printed circuit board (PCB) 67 inside the capsule 58 includes the necessary electronics for the imaging device. A camera lens 68 and image sensor 70 are integrated into the top housing 62 of the capsule 58. The lens 68 is mounted such that it overlies the image sensor 70 and focuses light entering the lens onto a photosensitive area of the image sensor. An integrated lens can be made by bonding the lens assembly onto the image sensor chip by means of optically inert glues such as Canada balsam.

Still referring to FIG. 9, in order to provide a light inside an abdominal cavity or other anatomical cavity of a patient, light sources 60, such as light emitting diodes (LEDs), are also integrated into the top component 62 of the capsule 58. The capsule 58 includes a hinge mechanism 72 to attach the capsule 58 to the distal portion of the cannula 12. This hinge mechanism 72 also allows the camera capsule 58 to exhibit movement in a single plane as illustrated in FIG. 8. This swivel mechanism 72 allows the camera capsule to be tucked inside the lumen 17 of the cannula 12 or to lie just outside of the lumen while the trocar 14 and cannula 12 are being inserted into an anatomical site.

Figure 2:
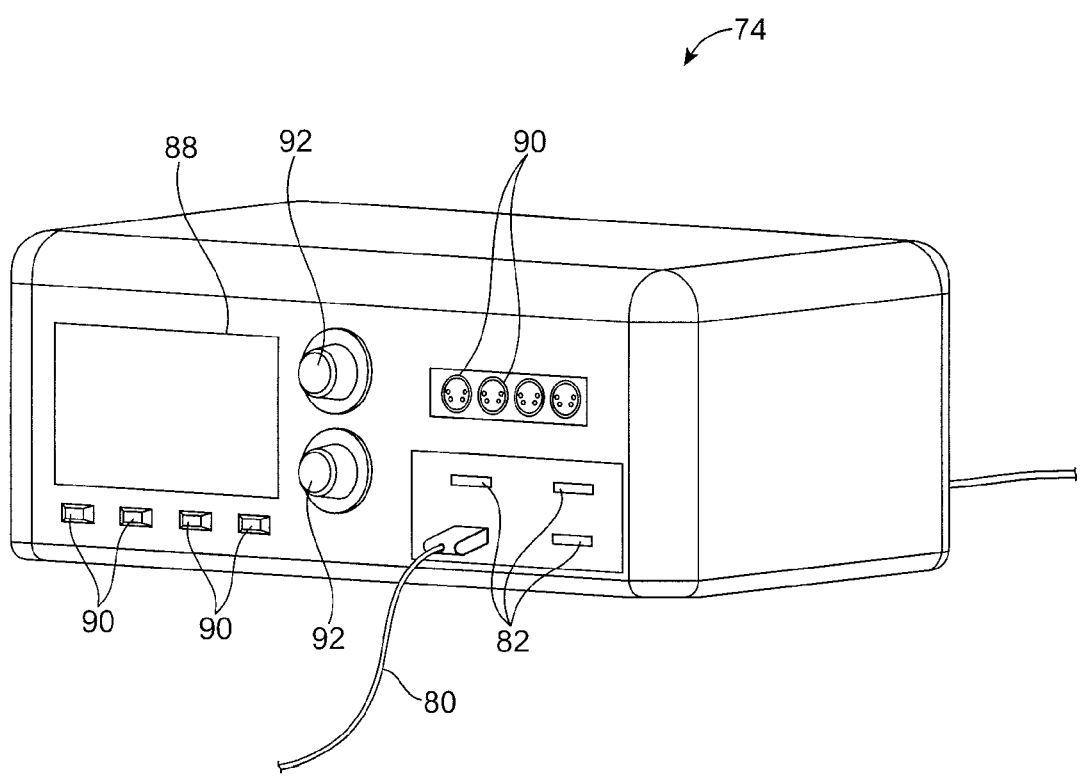
FIG. 2 is a perspective view of a control box in communication with the camera.

Preferably, but not necessarily, other electrical components are found in the camera capsule 58 and the control box 74 (FIG. 2).

Figure 10:
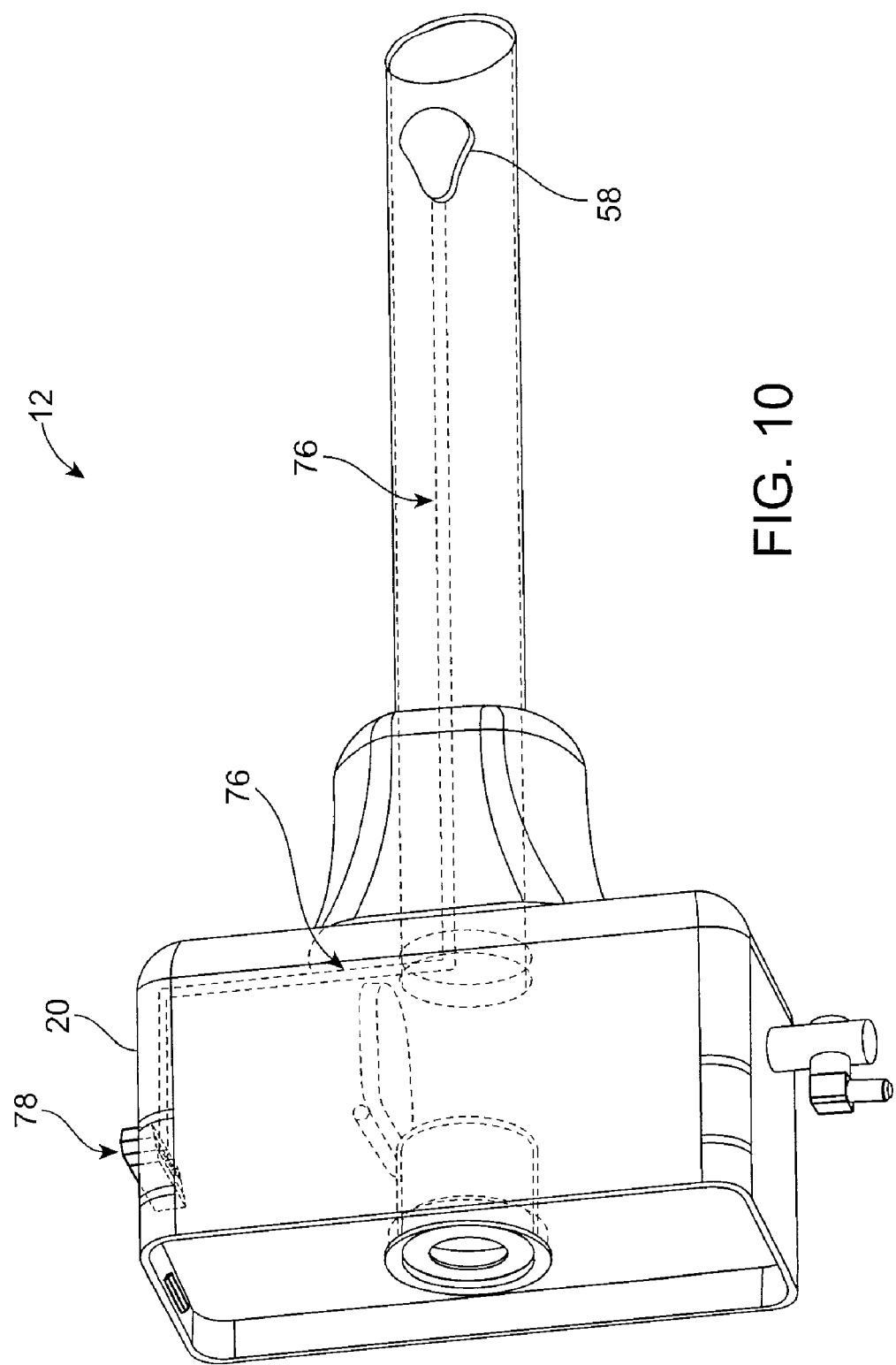
FIG. 10 is a perspective view of the cannula showing an electrical wire conduit inside the cannula, the conduit extending between the camera capsule and a connector on the cannula handle.

As shown in FIG. 10, electrical wiring from the camera capsule 58 is carried to the proximal end of the cannula through a conduit 76 and is interfaced to a connector 78 at the cannula handle 20. A cable assembly 80 (FIG. 2) routes these electrical connections to the control box 74 (FIG. 2) through one of the connectors 82 provided on the control box. The electrical wiring includes power, data/signal, and control lines. Power and control commands are received through the respective wires from the control box 74, and the data/signal line carries the video images to the control box.

Referring again to 9, the PCB 57 within the camera capsule 58 includes a power management integrated circuit (IC) 130, a clock or crystal 132, and a signal processing IC 134.

Figure 11:
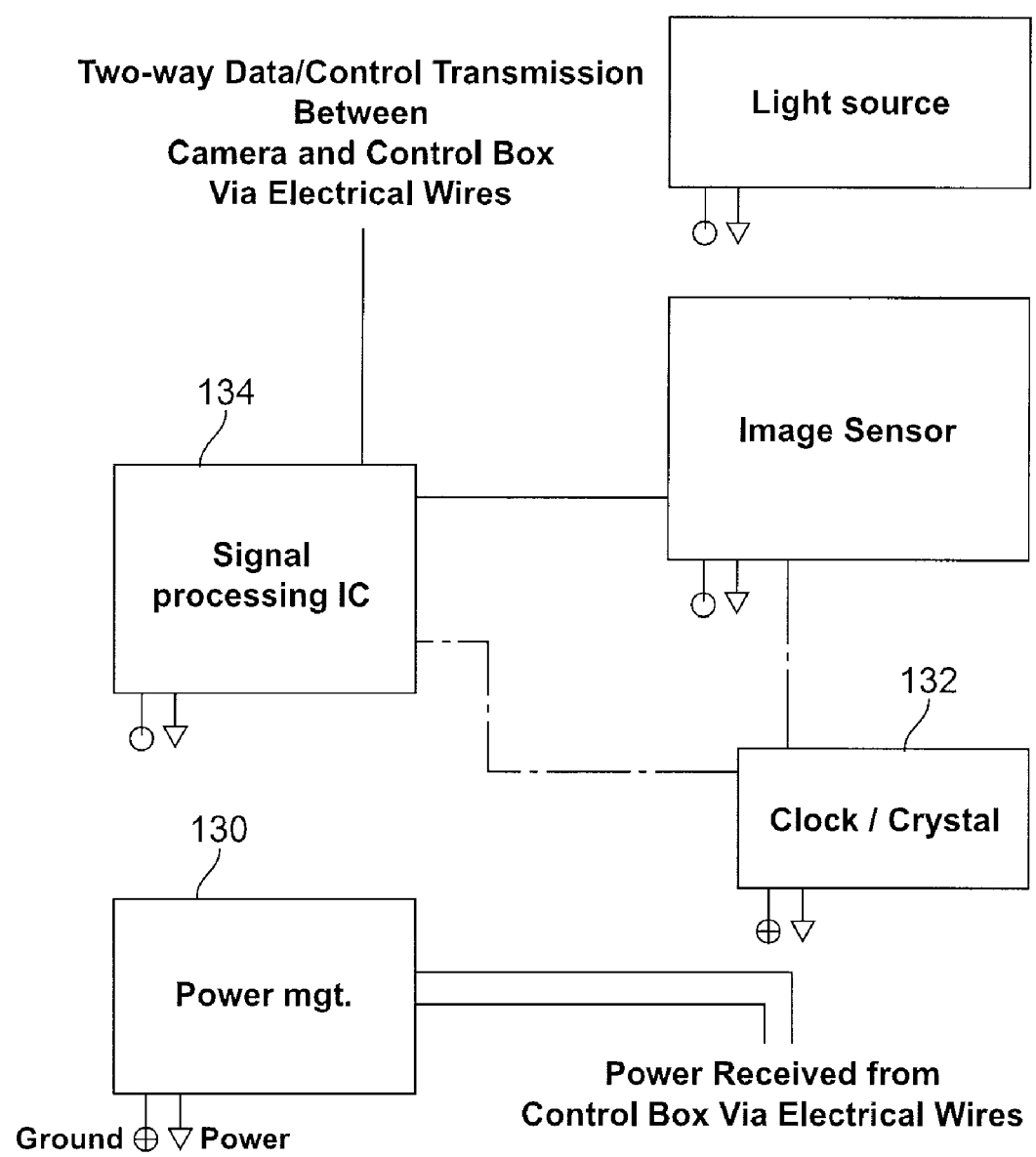
FIG. 11 is a block diagram of circuitry of the camera capsule.

In FIG. 11, there is shown a block diagram of circuitry within the camera capsule 58. Electrical wires 84 (FIG. 9) connect the PCB 57 to the image sensor 70 and LEDs 60, which are integrated into the capsule 58. Power to the light sources 60 is routed via the power management circuit 130 on the camera capsule PCB 57. Controlling circuitry may be included in this PCB 57 for adjusting the intensity of the light. This can be achieved by using a device such as a LED driver which can be controlled via the same or separate control line depending on the control technique employed.

The image sensor 70 integrated into the top housing 62 of the capsule 58, as shown in FIG. 9, is an electronic device which converts light incident on photosensitive semiconductor elements into electrical signals. The signals from the sensor 70 are digitized and used to reproduce the image that was incident on the sensor. Two types of image sensors 70 are Charge Coupled Devices (CCD) and Complementary Metal Oxide Semiconductor (CMOS) camera chips.

The image data captured by the image sensor 70 is then decoded by the signal processing integrated circuit 86 (FIG. 9). The variety of image sensor output formats and video signal processing integrated circuits is well documented and understood in the consumer electronics industry, and so this process is not explained in further detail. Once the signal has been converted to a suitable format, it is transferred to the control box 74 (FIG. 2).

Referring again to FIG. 2, the control box 74 transmits power and control commands from its internal circuitry to the camera capsule 58 near the distal end of the cannula 12. The control box 74 also serves to process and retransmit the video streams received from the camera capsule 58 to a display device, such as an LCD display 88 on the control box 74 or a video monitor connected to video output connectors 90 on the control box.

Figure 12:
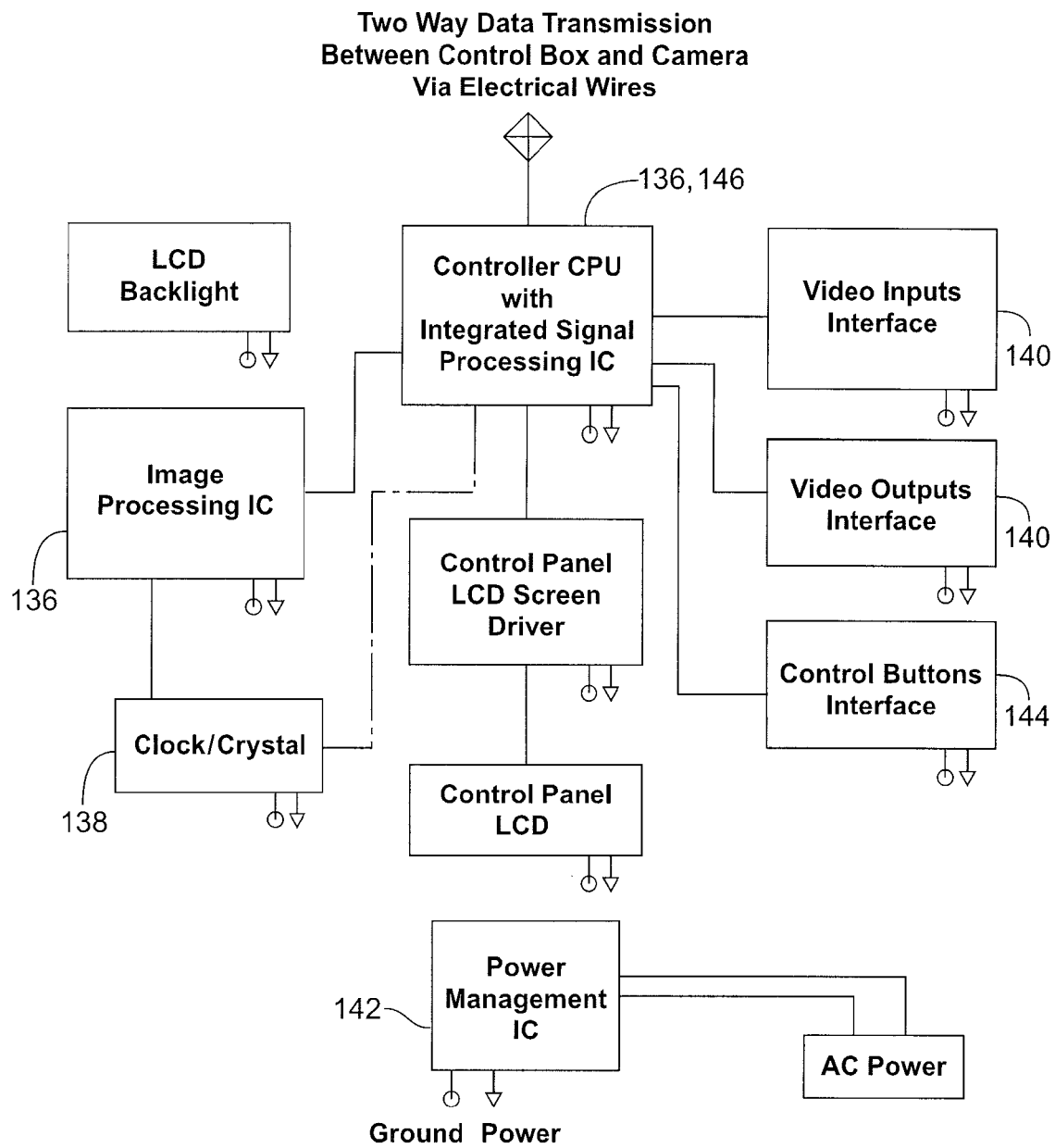
FIG. 12 is a block diagram of circuitry of the control box.

The control box 74 comprises of image and signal processing circuitry in an enclosure with a control panel, LCD display 88, and connectors. The LCD display 88 in conjunction with the control panel provides a menu-driven interface. FIG. 2 shows the physical layout of the control box 74, while FIG. 12 shows a block diagram of the circuitry of the control box. It will be appreciated that the control box 74 can be configured in ways other than what is shown in FIG. 2.

As shown in FIG. 12, the control box 74 comprises image and signal processing Ics 136, a crystal or clock 138, input and output interfaces 140, a power management IC 142, button input switches 144, and a controller CPU 146. After the control box 74 receives the signal from the camera 16, the controller CPU 146, which includes a signal processing IC, decodes the signal and is sent to image processing circuits 136. These circuits process the video signal in order to enhance image quality, extract still images, and convert the video format to other output formats. Once the video images have been processed, they are sent back to the controller CPU 146 for output to an external monitor.

Still referring to FIG. 12, the controller CPU 146 also interfaces with the image sensor 70 of the camera capsule 58. This CPU allows users to employ the buttons 92, knobs 94, and a menu-driven interface of the control box 74 (FIG. 2) to control mode settings, brightness, and exposure time by writing digital commands to specific registers controlling each of these parameters on the image sensor of the camera. These registers can be addressed by their unique addresses, and digital commands can be read from and written to these registers to change the different parameters.

Figure 13:
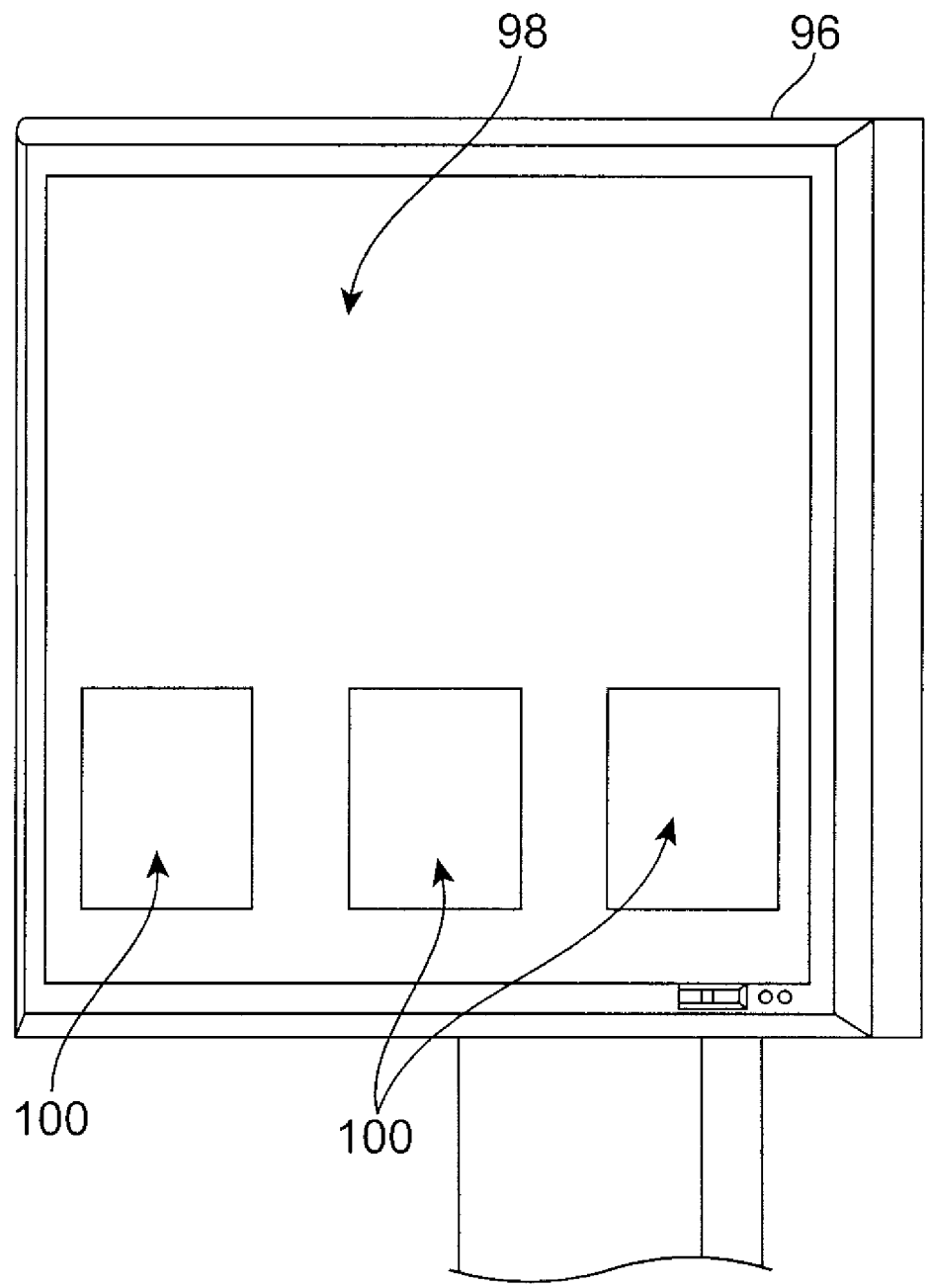
FIG. 13 is a perspective view of a display monitor in communication with the control box showing a main screen picture capable of showing a main view from a camera on a main access port and smaller pictures within the main screen picture capable of showing ancillary views from cameras on ancillary access ports.

The control box 74 has the capability to connect with multiple laparoscopy port camera systems simultaneously. The video signals from these multiple cameras can then be displayed on multiple displays or on a single display monitor 96 using a split-screen or picture-in-picture (PIP), as shown in FIG. 13. A view of the main endoscope can be shown on the main portion 98 of the display monitor 96, while additional views from various camera capsules can be shown as smaller pictures 100 within the main portion of the display.

Operation of the system shown in FIGS. 1-13 will now be described in accordance with an embodiment of the present invention. The electrical cable 80 between the cannula handle 20 and control box 74 is connected to the appropriate connectors 78, 82. The camera capsule 58 in the distal portion of the cannula 12 is pivoted outward by hand to the outside of the cannula lumen. The trocar 14 is then slid into the cannula 12 until the trocar handle 40 snaps into the cannula handle 20.

The camera 16 is then powered on by manipulating controls found on the control box 74. The camera 16 begins to transmit video images to the control box 74 through the electrical wires in the cannula 12. The internal circuitry of the control box 74 decodes and processes the signal in order to create video signals for output to an external monitor 96. The images are then displayed on the external monitor 96.

Before inserting the cannula 12 and trocar 14 into a patient, the camera capsule 58 is pivoted inward by hand into the lumen 17 of the cannula 12 in order to facilitate insertion. The cannula 12 and trocar 14 are pushed through the abdominal wall or other anatomical region by taking advantage of the cutting surface 50 on the distal tip of the trocar.

Once the anatomical region has been entered, the trocar 14 is withdrawn, leaving the cannula 12 in place. The larger diameter 47 of the distal tip of the trocar 14 causes the camera capsule 58 to pivot outward to its outside the lumen position. Under direct visualization through its camera 16, the cannula 12 is then carefully advanced to the appropriate depth. The cannula 12 is then ready to accept instruments through the cannula lumen 17.

Additional cannulas or access ports having cameras can be employed and connected to the same control box 74. Through the use of buttons on the control box 74, the user can vary brightness and other settings. The user can also obtain still images by pressing various buttons on the control box 74. After the surgery is completed, the access ports are simply withdrawn and associated cable connections are disconnected. As the access ports are withdrawn, pressure and frictional forces acting on the sides cause the camera capsules to pivot back to their inside the lumen position. The access ports are then discarded along with the trocars.

Figure 14:
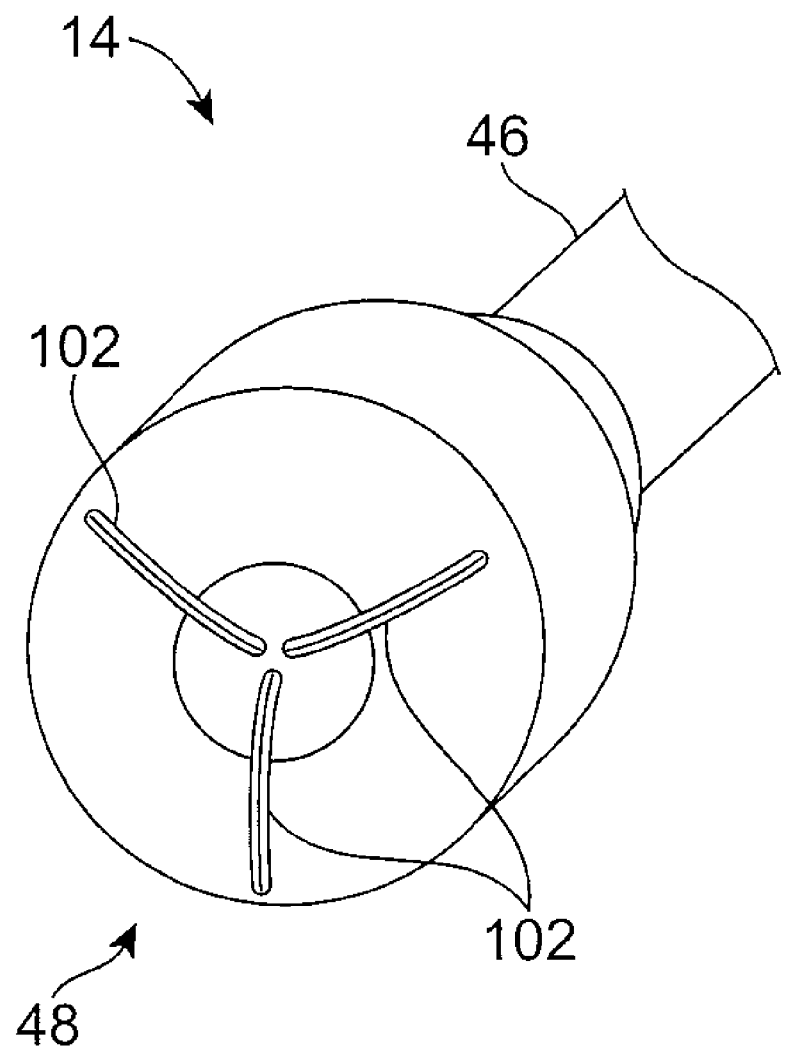
FIG. 14 is a perspective view of a trocar having three projection features at a distal tip of the trocar for facilitating entry of the trocar into an anatomical site.

In some embodiments of the present invention, a trocar has a blunt tip, instead of a sharp tip, to minimize the risk of injuring organs beneath the insertion point. In other embodiments, a trocar 14 has a distal tip 48 with three projections 102 made from plastic or metal, as shown in FIG. 14. The projections 102 are spaced equally around a center point on the distal tip 48 of the trocar 14.

In other embodiments of the present invention, a camera capsule is integrated at a point on the cannula that is more proximal or distal than is shown in FIGS. 1, 3, 4, 8, and 10. The hinge connector, which attaches the capsule to the cannula, can also be varied in order to provide a range of pivot angles.

Figure 15:
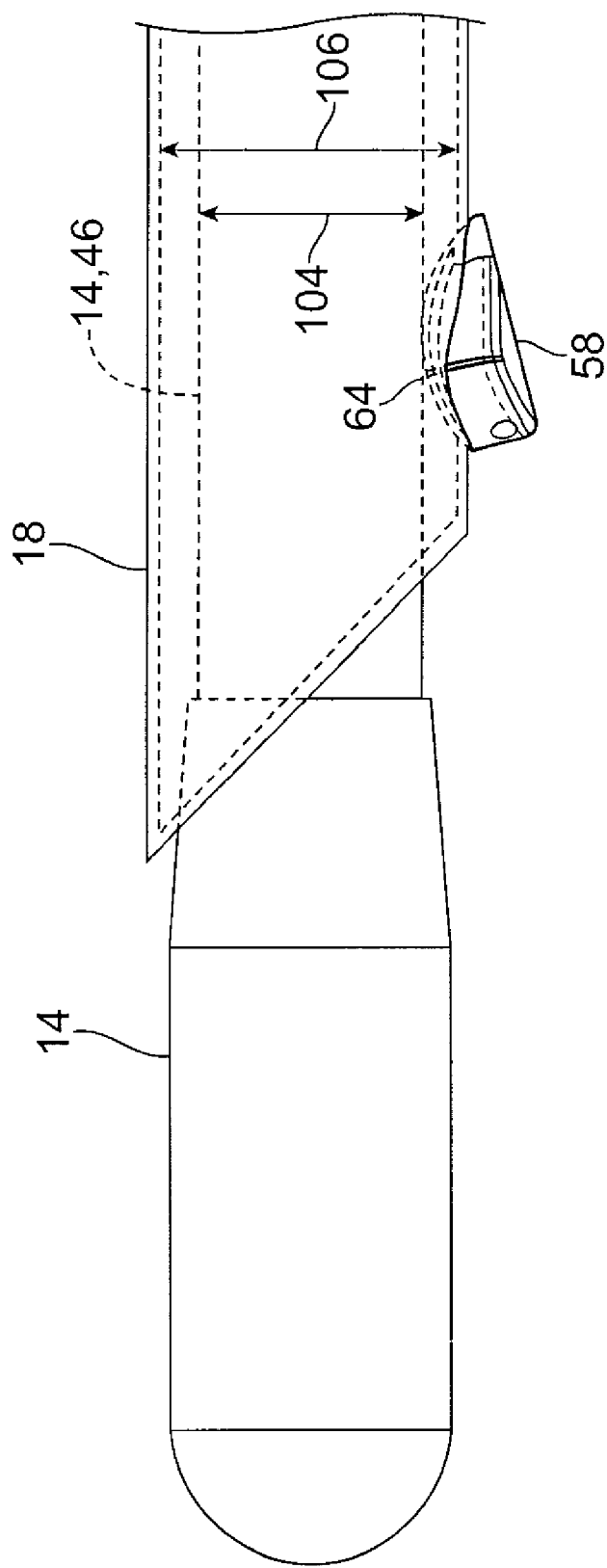
FIG. 15 is a close-up side view of a distal region of an access port assembly showing a blunt tip trocar inserted through an instrument passageway of an access port sleeve, and showing an integrated camera on the access port sleeve disposed outside an outer surface of the sleeve due to contact with a distal portion of the blunt tip trocar, the distal portion having a larger diameter than the medial portion of the trocar of FIG. 8.

In FIG. 15 there is shown an embodiment in accordance with the present invention in which a blunt tip trocar 14 is used to keep a camera capsule 58 in its "outside lumen position" even when there is no surgical instrument inserted through the access port sleeve 18. Instead of the narrow shaft 46 of FIG. 8, which allows the camera capsule 58 to lie in its "inside lumen position" during insertion of the cannula 12 and trocar 14 through an abdominal wall, the shaft 46 of FIG. 15 has an outside diameter 104 that is only slightly smaller than the inside diameter 106 of the access port sleeve 18. Therefore, the trocar of FIG. 15 exerts pressure on the bottom housing 64 of the camera capsule 58, thus maintaining the camera capsule in its "outside lumen position" so that the camera capsule can provide visualization of the surgical site for the duration of the procedure, even when there is no surgical instrument inserted through that port. The shaft 46 could have this larger diameter 104 throughout its full length, or only in that portion of the shaft where it would be required in order to exert pressure on the camera capsule 58 to maintain the camera capsule in its outside lumen position. The handle of the blunt tip trocar of FIG. 15 can be similar to that of the trocar used to facilitate insertion of the cannula, including projection features that mate with complimentary grooves found on the corresponding sections of the handle of the cannula.

In other embodiments of the present invention, a camera capsule is connected to a detent mechanism that, once the camera capsule has been swiveled into its outside lumen position through pressure from the tip of the trocar during withdrawal of the trocar, maintains the camera capsule in its outside lumen position for the duration of the surgical procedure, whether or not there is a trocar or other instrument occupying the lumen of the cannula. When the cannula is withdrawn, pressure and friction from the surrounding tissue of the abdominal wall will force the camera capsule to swivel past the detent mechanism and into its inside lumen position, thus facilitating withdrawal of the cannula while preventing trauma to the surrounding tissue.

In another embodiment, the cannula includes a mechanical control preferably near the cannula handle which allows the user to adjust the pivot angle of the camera from outside the patient's body. Two pull wires are attached to the camera capsule, and a lever attached to these wires is manipulated in order to articulate the camera capsule.

Figure 16:
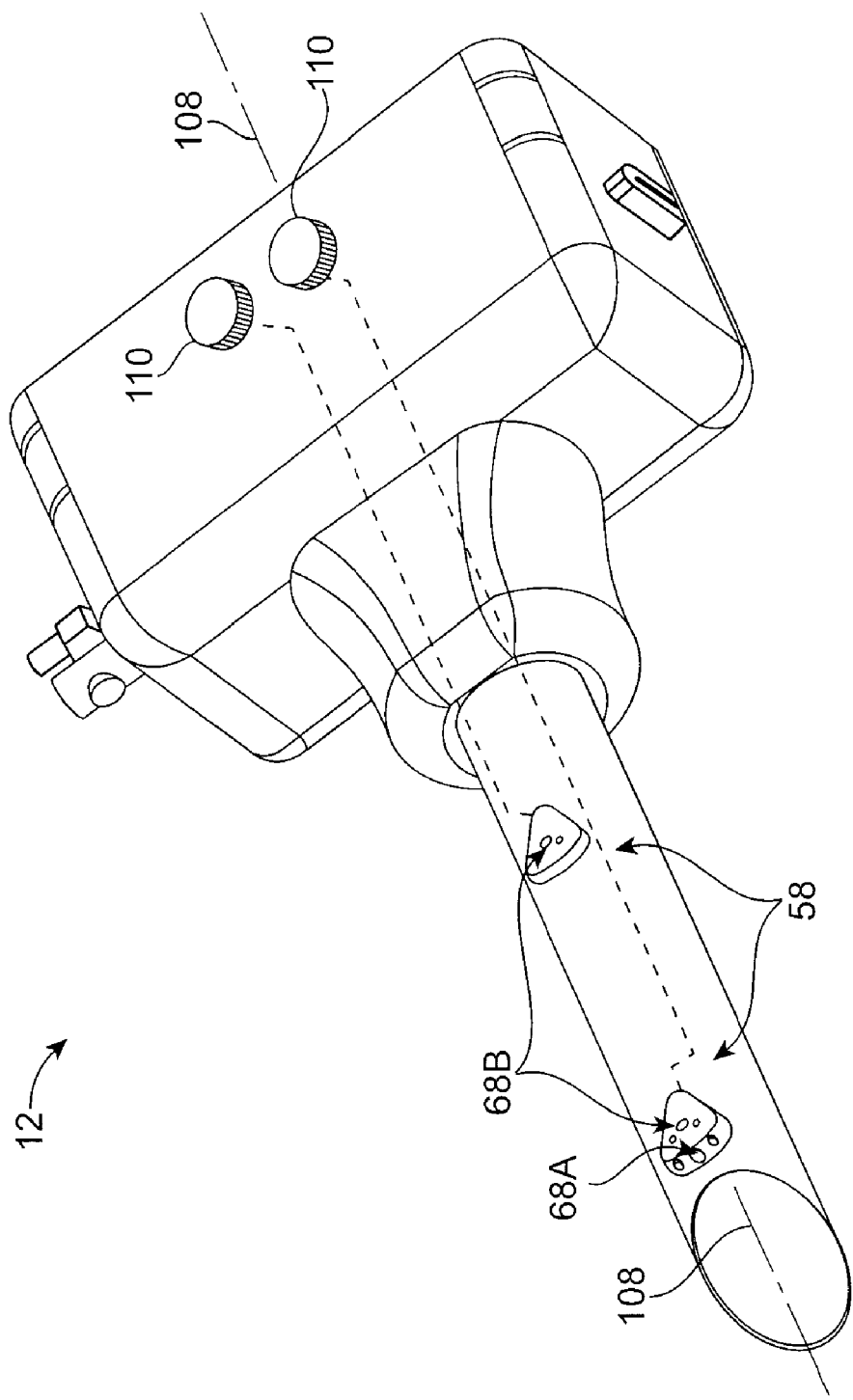
FIG. 16 is a perspective view of an access port showing a cannula sleeve, two cameras integrally mounted on the cannula sleeve, a cannula handle, and two controls on the handle adapted to allow for independent adjustment of camera viewing directions from between about zero degrees and about ninety degrees from a central axis of the cannula sleeve.

In FIG. 16, there is shown an embodiment of the present invention in which an access port 12 employs multiple camera capsules 58 with imaging lenses 68 that are oriented such that they can provide additional viewpoints. For example, one imaging lens 68A can be oriented longitudinally while other lens 68B can be oriented at a right angle to the longitudinal axis 108 of access port 12. This right angle view would provide an image that is especially useful for observing the exit ports of the other access ports during insertion and withdrawal of surgical instruments without requiring excessive manipulation of the access port 12. The two camera capsules 58 can be pivoted independently of one another to adjust its angle of view through an externally-controlled mechanism 110 without requiring movement of the entire access port 12.

Figure 17:
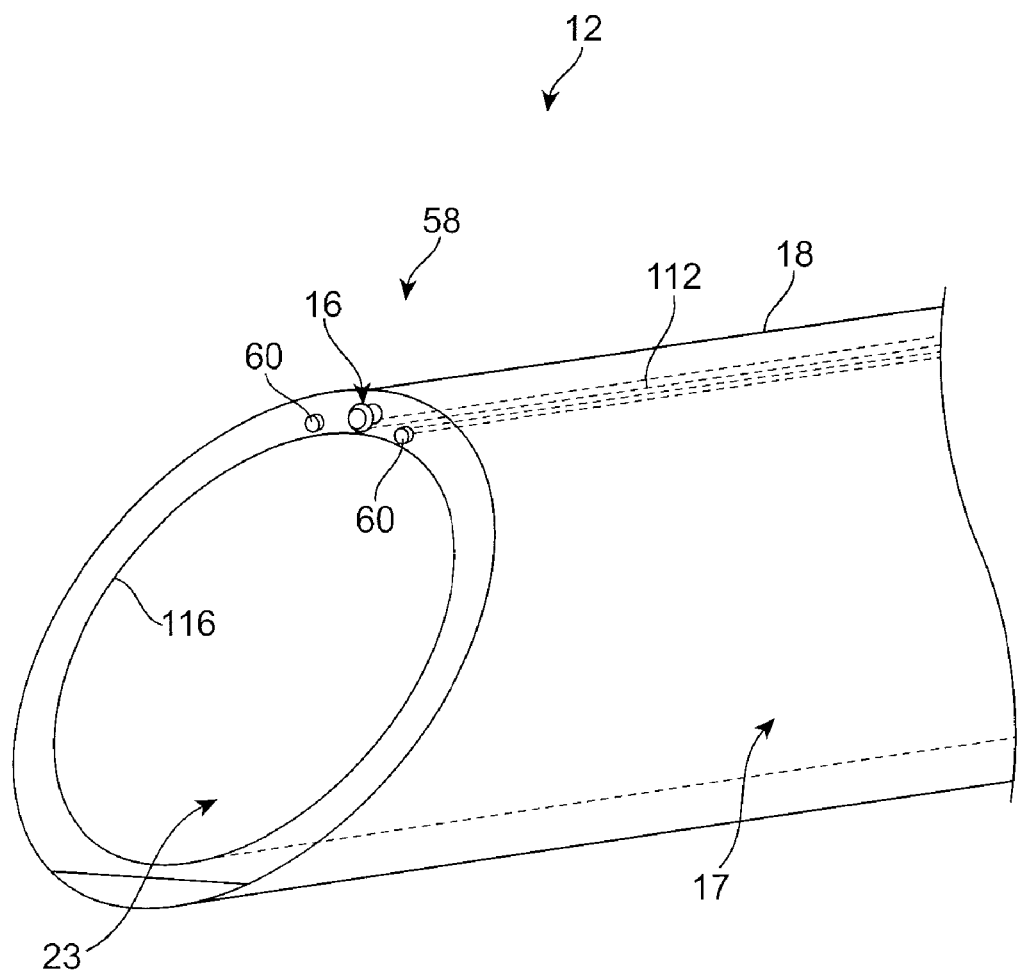
FIG. 17 is a perspective close-up view of an access port cannula showing an instrument exit opening at a distal end of the cannula, an instrument lumen extending from the exit opening, an imaging device disposed on a distal edge adjacent the exit opening, and an additional lumen housing the imaging device and imaging communication lines.

Referring now to FIG. 17, a camera capsule 58, which includes a camera 16 and light sources 60, is integrated into a cannula sleeve 18 having a small additional lumen 112 that houses the camera capsule and associated wires. The camera 16 and the light sources 60 are located on a distal edge 116 surrounding an exit port 23 of a cannula 12. The cylindrical component of the cannula 12 that houses the main instrument lumen 17 and the additional lumen 112 could be created by extruding a material such as polyethylene. In this embodiment, the camera 16 would be fixed in position, while the main lumen 17 would allow the passage of surgical instruments. Furthermore, this embodiment would allow visualization during insertion of the cannula 12 and trocar in order to prevent any accidental damage to tissue or organs.

Figure 18:
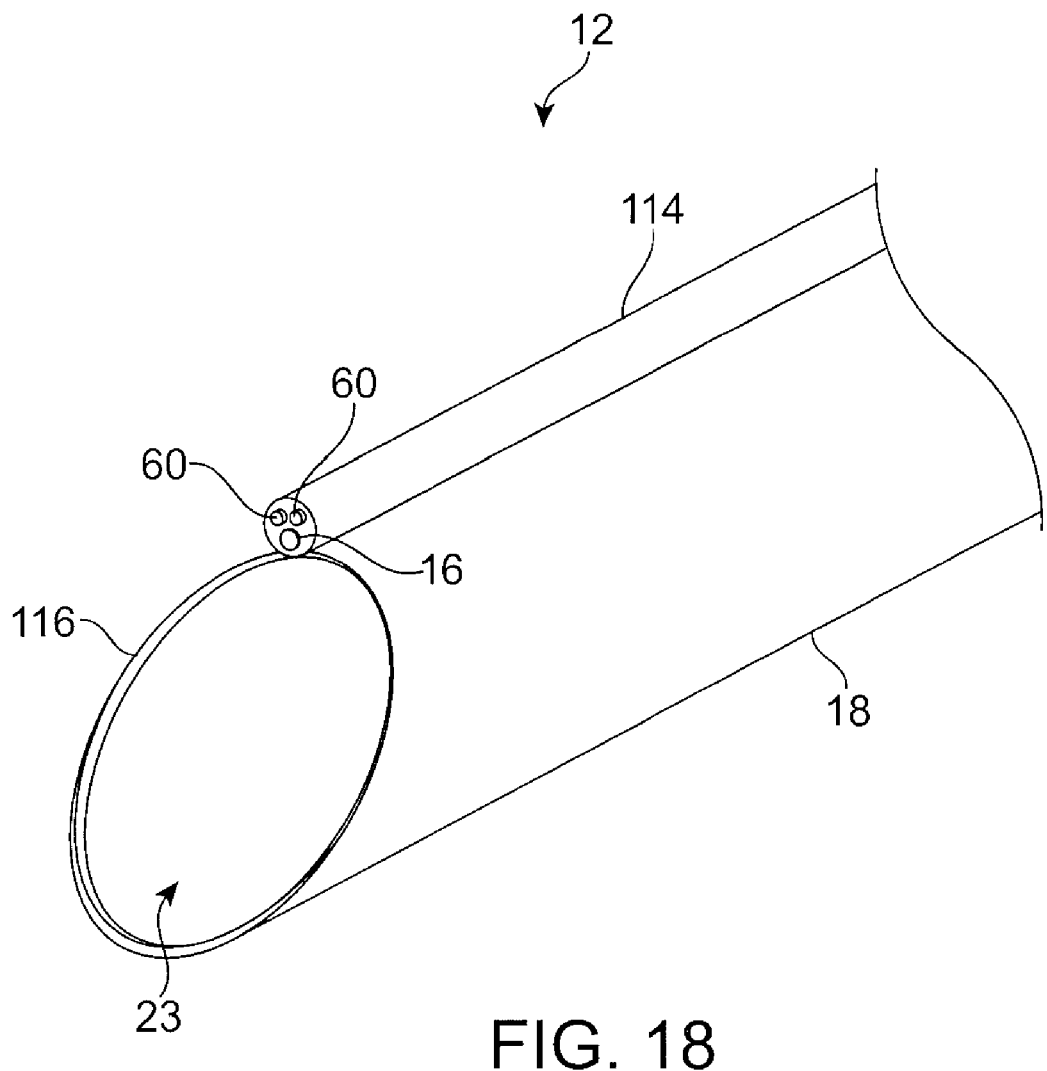
FIG. 18 is a perspective close-up view of an access port cannula showing an access port sleeve, an exterior channel disposed on an exterior surface of the sleeve, and an imaging device including two light sources and a camera disposed on a distal end of the exterior channel, the exterior channel housing imaging communication lines for the imaging device.

FIG. 18 depicts an embodiment in which a non-adjustable camera capsule 58 lies, along with its electrical wires, in a lumen or tube 114 that is external to the sheath 18 of a cannula 12. The camera capsule 58, which includes a camera 16 and two light sources 60, is adjacent a distal edge 116 surrounding an exit port 23 of the cannula 12. The tube 114 can be bonded to the outside surface of the cannula sheath 18 or simultaneously created with the sheath 18 by extruding a material such as polyethylene.

In another embodiment, an access port would employ an imaging lens located near the distal tip of the cannula. Fiber optic bundles embedded in the sheath of the cannula are employed to transfer images to an imaging sensor that may be located in the handle of the cannula. The imaging sensor receives the light signals and digitizes them for transfer to a video processing system and for display on a monitor or other output.

In yet another embodiment, an access port would not utilize embedded LEDs as a light source, but would instead employ one or more fiber optic bundles embedded in the sheath of the cannula to transfer light from an external source to the tip of the cannula to provide illumination of the surgical field.

Figure 19:
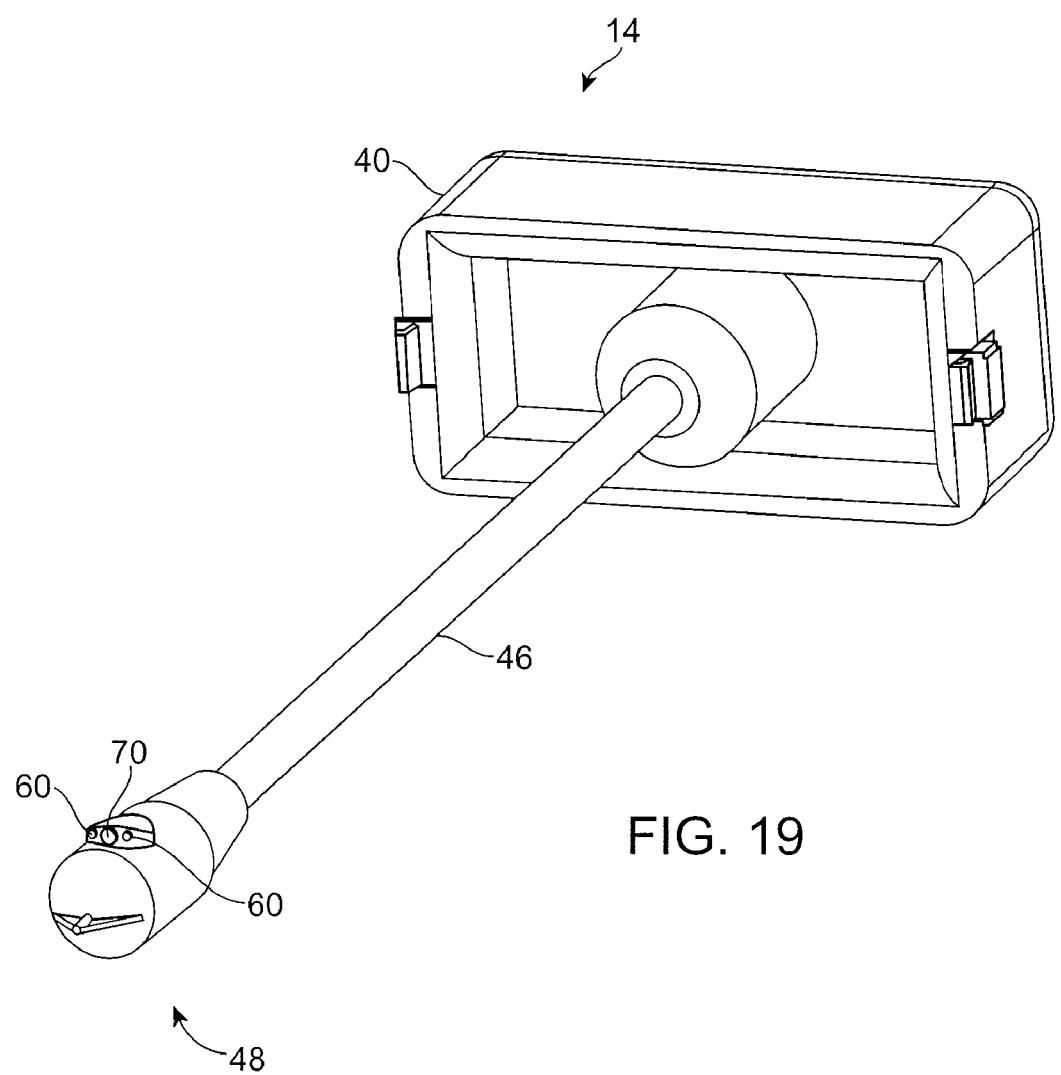
FIG. 19 is a perspective close-up view of an endoscopic device showing a handle connected by a shaft to a distal tip adapted to puncture an anatomical region and gain access to a surgical site, and an imaging device adjacent the distal tip.

FIG. 19 depicts an embodiment of the present invention in which a trocar 14, which is adapted to pass through a cannula, contains a light source 60, such as one or more LEDs or fiber optic bundles, as well as a sensor 70 with associated electrical wiring to transmit an image to a video processing system. The trocar 14 of FIG. 19 can extend a variable distance beyond the distal tip of the cannula in order to provide additional visualization of the surgical field, including close-up views.

In a further embodiments, a trocar can employ multiple camera capsules each having tenses and sensors that are oriented such that they can provide additional viewpoints. For example, one lens and sensor can be oriented longitudinally while another lens and sensor can be oriented at a right angle to a longitudinal axis of the trocar. This right angle view would provide an image that is especially useful for observing the exit ports of the other access ports during insertion and withdrawal of surgical instruments without requiring excessive manipulation of the trocar. The camera capsules can be pivoted to adjust their angle of view through an externally-controlled mechanism without movement of the trocar and its other camera capsules.

In other embodiments, imaging systems within a trocar employ imaging lenses located near the trocar distal tip. Fiber optic bundles embedded within the trocar transfer images from the imaging lenses to sensors located in the handle of the trocar. The sensor receive the light signals and digitize them for transfer to a video processing system and for display on a monitor or other output.

In further embodiments, a trocar includes an imaging device and one or more channels that can be used for water or saline irrigation, suctioning, or both, in order to further improve visualization of the surgical site.

In some embodiments, a cannula does not include electrical/communication wires connected to a camera capsule on the cannula. The camera capsule transmits data directly to an external control box by using a wireless protocol such as Bluetooth. A small battery is included in the camera capsule in order to power the electrical components. A wireless transceiver, which is responsible for transmitting the data at a given frequency, is found both in the camera capsule PCB and circuitry of the external control box.

In an other embodiments, an external control box includes PC connectivity. Video and still images can be stored onto internal memory. These images can then be transferred to external removable flash memory or transferred directly to a PC via serial communication protocols such as Universal Serial Bus (USB). The storage of images in memory and serial communication protocols such as USB are well documented and understood in the consumer electronics industry and so they will not be explained in further detail. Such an embodiment facilitates the inclusion of these video or still images in a patient's electronic medical record (EMR) by transferring the images to a personal computer. In addition, the image processing capabilities of the control box can convert the image and video data to a compatible format such as jpeg, mpeg, or others for filing in the patient's EMR. Furthermore, data can be retained in the control box for a duration of time by assigning a unique identifier to the corresponding images of each surgical procedure.

In some embodiments of the present invention, a cannula is be used independently of a trocar. A separate trocar or other puncturing or cutting device is utilized to make the incision. The cannula along with an integrated camera is then inserted into the incision. A camera capsule containing a camera can be articulated outward by inserting an instrument in the cannula lumen. Alternatively, a mechanical control with pull wires attached to the camera capsule can be employed to articulate the camera capsule.

Referring again to FIGS. 1 and 3, an endoscopic port assembly 10 is shown in accordance with an embodiment of the present invention. The endoscopic port assembly 10 can be used in a variety of endoscopic procedures. The endoscopic port assembly 10 comprises an endoscopic port 12, a trocar 14, and an imaging device 16. The port 12 includes a lumen 17. The trocar 14 is sized to be insertable into the lumen 17. The imaging device 16 is disposed on the port 12. The imaging device 16 may optionally be disposed on the trocar 14.

Referring next to FIG. 8, the port 12 of the endoscopic port assembly 10 may include a cannula or tubular member 18 to which the imaging device 16, 58 is mounted in a manner such that the imaging device is movable between a radially inward position (illustrated with broken lines) and a radially outward position (illustrated with in solid lines). Radially inward refers to a direction toward a longitudinal, central axis 118 of the tubular member 18, such as shown by directional arrow 120. Radially outward refers to a direction away from the central axis 118, such as shown by directional arrow 122.

Referring again to FIGS. 3-4, a laparoscopic device is shown in accordance with an embodiment of the present invention. The laparoscopic device is useful for providing minimally invasive access to organs within the peritoneal cavity of a patient. The laparoscopic device comprises a laparoscopic port 12 that includes an integrated imaging device 16. The port 12 preferably includes a cannula or tubular sheath 18 to which the imaging device 16 is mounted. The imaging device 16 is mounted such that an imaging lens of the imaging device is movable between a position outside the cannula 18 and a position inside the cannula. Optionally, the imaging device 16 is mounted such that the imaging lens is disposed at a distal edge 116 of the cannula 18.

Referring once again to FIGS. 5 and 8, an endoscopic port assembly 12 is shown in accordance with an embodiment of the present invention. The assembly 12 comprises an endoscopic port 12 and an imaging device 58. The port 12 includes a proximal end 22 and a distal end. An instrument passageway 17 extends from the proximal and distal ends. A first seal 28 is movable between an open position (illustrated with in solid lines) at which air may flow through the passageway and a closed position (illustrated with broken lines) at which air flow through the passageway from the distal end to the proximal end is blocked. The first seal 28 is adapted to move to the open position when an instrument 14 is inserted into the passageway 17. The first seal 28 is further adapted to move to the closed position when the instrument 14 is subsequently removed from the passageway 17. The port 12 also includes a second seal 26 that is adapted to block air flow through the passageway 17 when the instrument 14 is inserted into the passageway.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An endoscopic port assembly comprising:
    an endoscopic port including a lumen, a portion of the lumen including a tubular wall;
    a trocar sized to be insertable into the lumen, wherein the trocar includes a shaft, there being a gap between the shaft and the tubular wall when the trocar is inserted into the lumen; and
    an imaging device movably mounted to the tubular wall of the portion of the lumen, wherein the gap is sized to receive at least a portion of the imaging device, the trocar including a distal tip region connected to the shaft, the distal tip region being wider than the shaft such that, when the trocar is removed from the port, the distal tip region pushes the portion of the imaging device disposed within the gap such that the imaging device moves in a radially outward direction from the tubular wall.

2. The endoscopic port assembly of claim 1, wherein the port further includes a handle at a proximal end of the port and a cannula at a distal end of the port, the imaging device being disposed on the cannula.

3. The endoscopic port assembly of claim 1, wherein the imaging device includes either one or both of an imaging sensor and a light source.

4. The endoscopic port assembly of claim 1, wherein the port further includes a cannula, and wherein the imaging device is mounted on the cannula and is movable between a radially inward position and a radially outward position.

5. The endoscopic port assembly of claim 4, wherein the imaging device includes an imaging lens that is inside the cannula when the imaging device is in the inward position and is outside the cannula when the imaging device is in the outward position.

6. The endoscopic port assembly of claim 4, further comprising a detent mechanism that holds the imaging device in the outward position until the imaging device is pushed toward the inward position.

7. The endoscopic port assembly of claim 1, further comprising a movable control member that is connected to the imaging device such that manipulation of the control member moves the imaging device.

8. The endoscopic port assembly of claim 1, wherein the imaging device is attached to the trocar such that the imaging device extends beyond the distal end of the port when the trocar is inserted into the lumen.

9. The endoscopic port assembly of claim 1, further comprising a controller in communication with the imaging device, the controller providing power and control commands to the imaging device, the controller receiving image signals from the imaging device.

10. The endoscopic port assembly of claim 9, wherein the controller and the imaging device each include a wireless transceiver.

11. A laparoscopic device comprising:
    a laparoscopic port including a lumen, a portion of the lumen including a tubular wall;
    a trocar sized to be insertable into the lumen, wherein the trocar includes a shaft, there being a gap between the shaft and the tubular wall when the trocar is inserted into the lumen; and
    an imaging device movably mounted to the tubular wall of the portion of the lumen, wherein the gap is sized to receive at least a portion of the imaging device, the trocar including a distal tip region connected to the shaft, the distal tip region being wider than the shaft such that, when the trocar is removed from the port, the distal tip region pushes the portion of the imaging device disposed within the gap such that the imaging device moves in a radially outward direction from the tubular wall.

12. The laparoscopic device of claim 11, wherein the imaging device includes either one or both of an imaging sensor and a light source.

13. The laparoscopic device of claim 11, wherein the port includes a handle and a cannula connected to the handle, the handle having an instrument entry opening in communication with an instrument exit opening at a distal tip of the cannula.

14. The laparoscopic device of claim 13, wherein the imaging device includes an imaging lens and is mounted to the cannula such that the lens is movable between a position outside the cannula and a position inside the cannula.

15. The laparoscopic device of claim 13, wherein the imaging device includes an imaging lens disposed at a distal edge of the cannula.

16. The laparoscopic device of claim 13, wherein the cannula defines at least a portion of an instrument passageway extending from the instrument entry opening to the instrument exit opening.

17. The laparoscopic device of claim 16, wherein the cannula includes the lumen housing the imaging device.

18. The laparoscopic device of claim 16, wherein the cannula includes the lumen capable of providing irrigation, suction, or both.

19. An endoscopic port assembly comprising:
an endoscopic port including a proximal end, a distal end, an instrument passageway extending between the proximal and distal ends, and a first seal disposed within the passageway, a portion of the instrument passageway including a tubular wall, the first seal movable between an open position at which air may flow through the passageway and a closed position at which air flow through the passageway from the distal end to the proximal end is blocked;
a trocar sized to be insertable into the instrument passageway, wherein the trocar includes a shaft, there being a gap between the shaft and the tubular wall when the trocar is inserted into the instrument passageway; and
an imaging device movably mounted to the tubular wall of the portion of the instrument passageway, wherein the gap is sized to receive at least a portion of the imaging device, the trocar including a distal tip region connected to the shaft, the distal tip region being wider than the shaft such that, when the trocar is removed from the port, the distal tip region pushes the portion of the imaging device disposed within the gap such that the imaging device moves in a radially outward direction from the tubular wall.

20. The endoscopic port assembly of claim 19, wherein the first seal is adapted to move to the open position when an instrument is inserted into the passageway and to move to the closed position when the instrument is removed from the passageway.

21. The endoscopic port assembly of claim 19, wherein the port further includes a second seal adapted to block air flow through the passageway when an instrument is inserted into the passageway.

22. The endoscopic port assembly of claim 19, wherein the imaging device includes either one or both of an imaging sensor and a light source.

23. The endoscopic port assembly of claim 19, wherein the imaging device includes a lens and is movably mounted to allow the lens to be adjustably oriented at an angle between about zero degrees and about ninety degrees from a central axis of the tubular wall.

24. The endoscopic port assembly of claim 19, wherein the imaging device includes a lens located at a distal edge of the tubular wall.

* * * * *